(12) United States Patent
Leblanc et al.

(10) Patent No.: US 8,546,422 B2
(45) Date of Patent: Oct. 1, 2013

(54) AZAINDOLE DERIVATIVES AS CRTH2 RECEPTOR ANTAGONISTS

(75) Inventors: Yves Leblanc, Kirkland (CA); Carl Berthelette, Ste Dorothee Laval (CA); Daniel Simard, Brookline, MA (US); Mohamed Helmi Zaghdane, Montreal (CA)

(73) Assignee: Merck Canada Inc., Kirkland, Quebec (CA)

( * ) Notice: Subject to any disclaimer, the term of this patent is extended or adjusted under 35 U.S.C. 154(b) by 317 days.

(21) Appl. No.: 13/120,067

(22) PCT Filed: Sep. 17, 2009

(86) PCT No.: PCT/CA2009/001322
§ 371 (c)(1),
(2), (4) Date: Mar. 21, 2011

(87) PCT Pub. No.: WO2010/031184
PCT Pub. Date: Mar. 25, 2010

(65) Prior Publication Data
US 2011/0178115 A1   Jul. 21, 2011

Related U.S. Application Data

(60) Provisional application No. 61/192,736, filed on Sep. 22, 2008, provisional application No. 61/172,414, filed on Apr. 24, 2009.

(51) Int. Cl.
C07D 491/00 (2006.01)
C07D 498/00 (2006.01)
C07D 513/00 (2006.01)
C07D 515/00 (2006.01)
C07D 471/00 (2006.01)

(52) U.S. Cl.
USPC ............................. 514/292; 546/86; 546/87

(58) Field of Classification Search
CPC .. C07D 491/00; C07D 498/00; C07D 513/00; C07D 515/00; C07D 471/00
See application file for complete search history.

(56) References Cited

U.S. PATENT DOCUMENTS

| | | | |
|---|---|---|---|
| 7,618,979 | B2 | 11/2009 | Leblanc et al. |
| 7,696,222 | B2 | 4/2010 | Wang |
| 2008/0292626 | A1 | 11/2008 | Wang et al. |
| 2010/0234415 | A1 | 9/2010 | Berthelette et al. |

FOREIGN PATENT DOCUMENTS

| | | | |
|---|---|---|---|
| CA | 2323720 C | | 4/2001 |
| CA | 2503767 C | | 5/2004 |
| WO | 2006125179 A1 | | 11/2006 |
| WO | 2007019675 A1 | | 2/2007 |
| WO | WO 2007019675 A1 | * | 2/2007 |
| WO | 2009049021 A1 | | 4/2009 |
| WO | WO 2009/049021 | * | 4/2009 |
| WO | WO 2009049021 A1 | * | 4/2009 |
| WO | 2010031182 A1 | | 3/2010 |
| WO | 2010131183 A1 | | 3/2010 |

OTHER PUBLICATIONS

Bit, Rino A., et al., "Inhibitors of Protein Kinase C. 3. Potent and Highly Selective Bisindolylmaleimides by Conformational Restriction," Journal of Medicinal Chemistry, 1993, vol. 36, pp. 21-29.
Bit, Rino A., et al., "A Dieckmann/Ring Expansion Approach to Tetrahydropyrido- and Tetrahydroazepino-[1,2-a] Indoles," Tetrahedron, 1991, vol. 47, No. 26, pp. 4645-4664.
Stearns, Brian A., et al, "Novel tricyclic antagonists of the prostaglandin D2 receptor DP2 with efficacy in a murine model of allergic rhinitis," Bioorganic & Medicinal Chemistry Letters, 2009, vol. 19, pp. 4647-4651.
International Search Report corresponding to PCT/CA2009/001322, issued Dec. 16, 2009.
International Preliminary Report on Patentability corresponding to PCT/CA2009/001322, issued Mar. 22, 2011.
Preliminary Amendment corresponding to U.S. National Stage of PCT/CA2009/001321, filed Sep. 17, 2009, which is U.S. Appl. No. 13/120,076.
Preliminary Amendment corresponding to U.S. National Stage of PCT/CA2009/001320, filed Sep. 17, 2009 which is U.S. Appl. No. 13/120,074.

* cited by examiner

*Primary Examiner* — Rita Desai
*Assistant Examiner* — Ben S Michelson
(74) *Attorney, Agent, or Firm* — Eric A. Meade; Valerie J. Camara

(57) ABSTRACT

Compounds of formula I are antagonists of the PGD2 receptor, CRTH2, and as such are useful in the treatment and/or prevention of CRTH2-mediated diseases such as asthma.

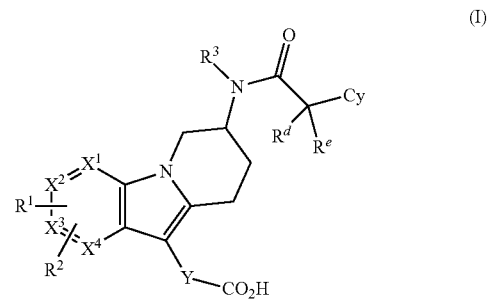

(I)

27 Claims, No Drawings

AZAINDOLE DERIVATIVES AS CRTH2 RECEPTOR ANTAGONISTS

BACKGROUND OF THE INVENTION

Prostanglandin $D_2$ ($PGD_2$) is a cyclooxygenase metabolite of arachidonic acid. It is released from mast and TH2 cells in response to an immunological challenge, and has been implicated in playing a role in different physiological events such as sleep and allergic responses.

Receptors for $PGD_2$ include the "DP" receptor, the chemoattractant receptor-homologous molecule expressed on TH2 cells ("CRTH2"), and the "FP" receptor. These receptors are G-protein coupled receptors activated by $PGD_2$. The CRTH2 receptor and its expression on different cells including human T-helper cells, basophils, and eosinophils are described in Abe, et al., *Gene* 227:71-77, 1999, Nagata, et al., *FEBS Letters* 459:195-199, 1999, and Nagata, et al., *The Journal of Immunology* 162:1278-1286, 1999, describe CRTH2 receptor. Hirai, et al., *J. Exp. Med.* 193:255-261, 2001, indicates that CRTH2 is a receptor for $PGD_2$.

WO2007019675 discloses CRTH2 antagonists of the formula:

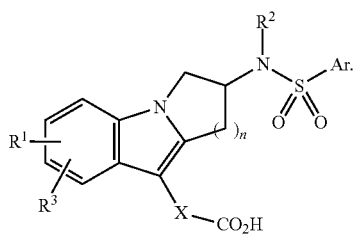

SUMMARY OF THE INVENTION

The present invention provides novel compounds which are CRTH2 receptor antagonists. Compounds of the present invention are useful for the treatment of various prostaglandin-mediated diseases and disorders; accordingly the present invention provides a method for the treatment of prostaglandin-mediated diseases using the novel compounds described herein, as well as pharmaceutical compositions containing them.

DETAILED DESCRIPTION OF THE INVENTION

The present invention relates to compounds of formula I:

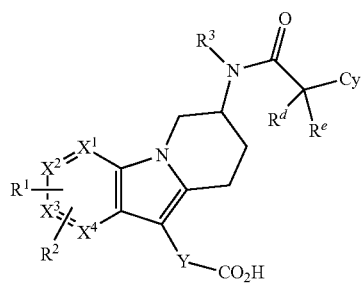

or a pharmaceutically acceptable salt thereof, wherein:
one of $X^1$, $X^2$, $X^3$ and $X^4$ is N and the others are CH;
Y is selected from $-C(R^a)(R^b)-$, $-C(R^a)(R^b)-C(R^a)(R^b)-$, $-C(R^a)=C(R^b)-$, $-OCH_2-$, $-OCH(C_{1-3}$ alkyl)-, $-OC(C_{1-3}$alkyl$)_2$-, $-OC(CH_2)_{2-5}-$, $-SCH_2-$, $-SCH(C_{1-3}$alkyl)-, $-SC(C_{1-3}$alkyl$)_2$- and $-SC(CH_2)_{2-5}-$;

Cy is aryl, heteroaryl or $C_{3-6}$ cycloalkyl optionally fused to a benzene, each of which is optionally substituted with 1 to 4 groups independently selected from $R^c$;

$R^1$ is selected from H, halogen, $-C_{1-6}$alkyl and $-OC_{1-6}$alkyl;

$R^2$ is selected from H, halogen, $-C_{1-6}$alkyl, $-SC_{1-6}$alkyl, $-S(O)C_{1-6}$alkyl, $-S(O)_2C_{1-6}$alkyl, $-CN$, aryl and heteroaryl;

$R^3$ is selected from H, $C_{1-6}$alkyl and benzyl optionally substituted on the phenyl portion with 1 to 3 halogen;

$R^a$ and $R^b$ are independently H, aryl, heteroaryl, $C_{1-6}$alkyl or halo$C_{1-6}$alkyl; or $R^a$ and $R^b$ together with the carbon atom to which they are both attached form a $C_{3-6}$cycloalkyl ring; or $R^a$ and $R^b$ together with the adjacent carbon atoms to which they are attached form a $C_{3-6}$cycloalkyl ring;

$R^c$ is selected from halogen, $NR^fR^g$, $SO_2NR^fR^g$, CN, $C_{1-6}$alkoxy, $C_{1-6}$alkyl, halo$C_{1-6}$alkoxy, and halo$C_{1-6}$alkyl;

$R^d$ and $R^e$ are independently selected from hydrogen, $C_{1-6}$alkyl, $-C_{1-6}$alkyl-$C_{3-6}$cycloalkyl, hydroxy, $C_{1-6}$alkoxy, aryl optionally substituted with 1 to 3 groups independently selected from $R^c$, and $NR^fR^g$; or $R^d$, $R^e$ together with the carbon atom to which they are both attached form a $C_{3-6}$cycloalkyl optionally having a ring heteroatom selected from $-O-$, $-S-$, $-N(C(O)R^f)-$ and $-N(R^f)-$, and optionally substituted with 1 to 3 $C_{1-3}$alkyl groups; and $R^f$ and $R^g$ are independently selected from hydrogen and $C_{1-3}$alkyl; or $R^f$, $R^g$ together with the atom to which they are both attached form a 3- to 6-membered ring.

In one subset of formula I are compounds wherein Cy is phenyl optionally substituted with 1 to 3 groups independently selected from $R^c$. In one embodiment thereof Cy is phenyl optionally substituted with 1 to 2 groups independently selected from halogen, $C_{1-6}$alkyl, halo$C_{1-6}$alkyl and $C_{1-6}$alkoxy.

In another subset of formula I are compounds wherein Y is $-C(R^a)(R^b)-$. In one embodiment thereof Y is methylene.

In another subset of formula I are compounds wherein Y is methylene; Cy is phenyl optionally substituted with 1 to 2 groups independently selected from halogen, $C_{1-6}$alkyl, halo$C_{1-6}$alkyl and $C_{1-6}$alkoxy. In one embodiment thereof, Cy is phenyl optionally substituted with 1 or 2 halogen atoms.

In another subset of formula I are compounds wherein the chiral carbon to which the $-NR^3-C(O)CR^dR^e$-Cy moiety is attached has the (R)-configuration.

In another subset of formula I are compounds of formula Ia or a pharmaceutically acceptable salt thereof:

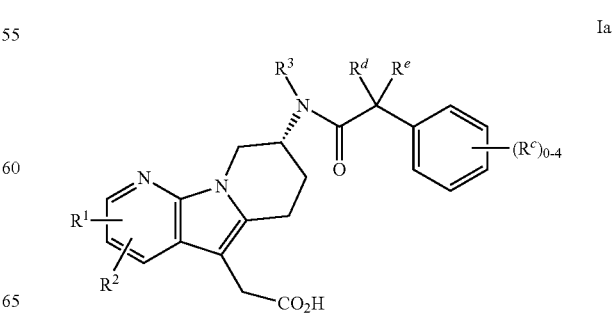

wherein $R^1$, $R^2$, $R^3$, $R^c$, $R^d$ and $R^e$ are as defined under formula I. In one embodiment thereof are compounds wherein $R^d$ and $R^e$ are independently selected from hydrogen and $C_{1-3}$alkyl, and $R^c$ is halogen; more particularly, at least one of $R^d$ and $R^e$ is $C_{1-3}$alkyl. In another embodiment $R^c$ is halogen, and —C($R^d$)($R^e$)— is selected from —CH(Ph)—,

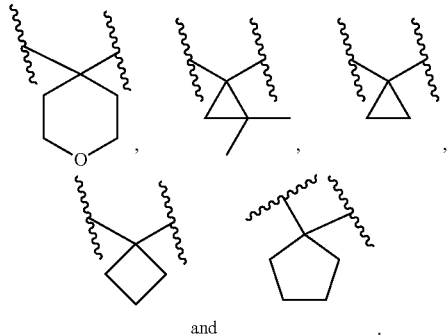

and

In another subset of formula I are compounds of formula Ib or a pharmaceutically acceptable salt thereof:

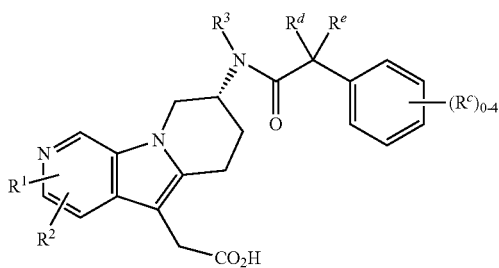

wherein $R^1$, $R^2$, $R^3$, $R^c$, $R^d$ and $R^e$ are as defined under formula I. In one embodiment thereof are compounds wherein $R^d$ and $R^e$ are independently selected from hydrogen and $C_{1-3}$alkyl, and $R^c$ is halogen.

In another subset of formula I are compounds of formula Ic or a pharmaceutically acceptable salt thereof:

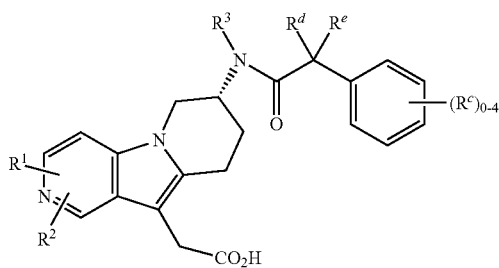

wherein $R^1$, $R^2$, $R^3$, $R^c$, $R^d$ and $R^e$ are as defined under formula I. In one embodiment thereof are compounds wherein $R^d$ and $R^e$ are independently selected from hydrogen and $C_{1-3}$alkyl, and $R^c$ is halogen.

In another subset of formula I are compounds of formula Id or a pharmaceutically acceptable salt thereof:

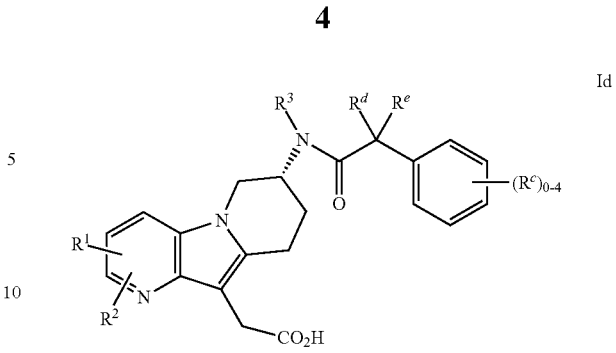

wherein $R^1$, $R^2$, $R^3$, $R^c$, $R^d$ and $R^e$ are as defined under formula I. In one embodiment thereof are compounds wherein $R^d$ and $R^e$ are independently selected from hydrogen and $C_{1-3}$alkyl, and $R^c$ is halogen.

In another subset of formula I are compounds of formula Ie or a pharmaceutically acceptable salt thereof:

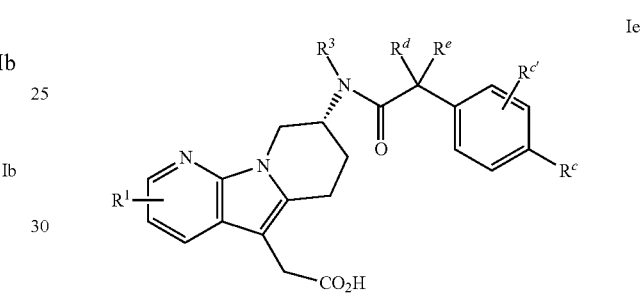

wherein $R^1$ and $R^3$ are as defined under formula I; $R^c$ is a halogen; $R^{c'}$ is hydrogen or a halogen; $R^d$ and $R^e$ are independently selected from hydrogen and $C_{1-3}$allyl, or $R^d$ and $R^e$ together with the carbon atom to which they are both attached form a $C_{3-6}$cycloalkyl or tetrahydropyranyl, each of which is optionally substituted with 1 to 2 $C_{1-3}$alkyl groups. In one embodiment $R^1$ and $R^{c'}$ are each hydrogen, and $R^3$ is methyl.

In another subset of formula I are compounds selected from the group consisting of:
((8R)-8-{methyl[(2R)-2-(4-fluorophenyl)propanoyl] amino}-6,7,8,9-tetrahydropyrido[3,2-b]-indolizin-5-yl) acetic acid;
((8R)-8-{methyl[(2S)-2-(4-fluorophenyl)propanoyl] amino}-6,7,8,9-tetrahydropyrido[3,2-b]-indolizin-5-yl) acetic acid;
{(8R)-8-[[2-(4-fluorophenyl)-3-methylbutanoyl](methyl) amino]-6,7,8,9-tetrahydropyrido[3,2-b]-indolizin-5-yl}acetic acid;
{(8R)-8-[(diphenylacetyl)(methyl)amino]-6,7,8,9-tetrahydropyrido[3,2-b]indolizin-5-yl}acetic acid;
{(8R)-8-[[2-(4-fluorophenyl)-2-methylpropanoyl](methyl) amino]-6,7,8,9-tetrahydropyrido-[3,2-b]indolizin-5-yl}acetic acid;
{(8R)-8-[{[4-(4-fluorophenyl)tetrahydro-2H-pyran-4-yl] carbonyl}(methyl)amino]-6,7,8,9-tetrahydropyrido[3,2-b]indolizin-5-yl}acetic acid;
{(8R)-8-[{[1-(4-fluorophenyl)-2,2-dimethylcyclopropyl] carbonyl}(methyl)amino]-6,7,8,9-tetrahydropyrido[3,2-b]indolizin-5-yl}acetic acid;
{(8R)-8-[{[1-(4-fluorophenyl)cyclobutyl]carbonyl}(methyl)amino]-6,7,8,9-tetrahydropyrido-[3,2-b]indolizin-5-yl}acetic acid; and {(8R)-8-[{[1-(4-fluorophenyl)cyclopentyl]carbonyl}(methyl)amino]-6,7,8,9-tetrahydro-pyrido[3,2-b]indolizin-5-yl}acetic acid,
or a pharmaceutically acceptable salt thereof In another aspect the present invention relates to compounds of formula II:

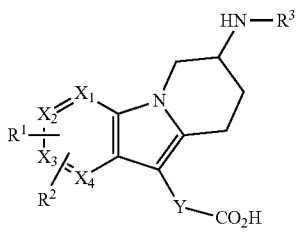

or a salt or a $C_{1-6}$alkyl ester thereof, wherein the variables are as defined under formula I. In one subset of formula II are compounds wherein $X^1$ is N, and $X^2$, $X^3$ and $X^4$ are each CH; $R^1$ and $R^2$ are each H; and Y is —$CH_2$—. Compounds of formula II are intermediates useful in the preparation of compounds of formula I, and encompass salts, esters or salts of esters thereof. Salts and esters may be any that are useful in the performance of the reaction(s) to arrive at compounds of formula I; salts include, but are not limited to, pharmaceutically acceptable salts; esters may be, for example, methyl, ethyl, n-propyl, isopropyl, n-butyl, s-butyl, t-butyl, and the like.

The invention also encompasses pharmaceutical compositions containing a compound of formula I, and methods for treatment or prevention of prostaglandin mediated diseases using compounds of formula I.

The invention is described using the following definitions unless otherwise indicated.

The term "halogen" or "halo" includes F, Cl, Br, and I.

The term "alkyl" refers to linear or branched alkyl chains having the indicated number of carbon atoms. Non-limiting examples of alkyl groups include methyl, ethyl, n-propyl, isopropyl, n-butyl, s- and t-butyl, pentyl, hexyl, and the like.

The term "cycloalkyl" refers to saturated carbocycles having the indicated number of ring carbon atoms, and includes cyclopropyl, cyclobutyl, cyclopentyl, cyclohexyl. A "cycloalkyl fused to a benzene" is a bicyclic carbocycle with no additional unsaturation other than in the benzene portion; examples include benzocyclobutenyl, indanyl and tetrahydronaphthyl.

"Haloalkyl" means an alkyl group as described above wherein one or more hydrogen atoms have been replaced by halogen atoms, with up to complete substitution of all hydrogen atoms with halo groups. $C_{1-6}$haloalkyl, for example, includes —$CF_3$, —$CF_2CF_3$, $CHFCH_3$, and the like.

"Alkoxy" means alkoxy groups of a linear or branched alkyl chain having the indicated number of carbon atoms. $C_{1-6}$alkoxy, for example, includes methoxy, ethoxy, propoxy, isopropoxy, and the like.

"Haloalkoxy" means an alkoxy group as described above in which one or more hydrogen atoms have been replaced by halogen atoms, with up to complete substitution of all hydrogen atoms with halo groups. $C_{1-6}$haloalkoxy, for example, includes —$OCF_3$, —$OCF_2CF_3$, —$OCH_2CF_3$ and the like.

"Aryl" means a 6-14 membered carbocyclic aromatic ring system comprising 1-3 benzene rings. If two or more aromatic rings are present, then the rings are fused together, so that adjacent rings share a common bond. Examples include phenyl and naphthyl.

The term "heteroaryl" (Het) as used herein represents a 5-10 membered aromatic ring system containing one ring or two fused rings, and 1-4 heteroatoms selected from O, S and N. Het includes, but is not limited to, furanyl, imidazolyl, isoxazolyl, isothiazolyl, oxadiazolyl, oxazolyl, pyrazolyl, pyridyl, pyrrolyl, tetrazolyl, thiazolyl, thiadiazolyl, thienyl, triazinyl, triazolyl, 1H-pyrrole-2,5-dionyl, 2-pyrone, 4-pyrone, pyrrolopyridine, furopyridine and thienopyridine.

"Therapeutically effective amount" means that amount of a drug or pharmaceutical agent that will elicit the biological or medical response of a tissue, a system, animal or human that is being sought by a researcher, veterinarian, medical doctor or other clinician.

The term "treatment" or "treating" includes alleviating, ameliorating, relieving or otherwise reducing the signs and symptoms associated with a disease or disorder.

The term "composition", as in pharmaceutical composition, is intended to encompass a product comprising the active ingredient(s), and the inert ingredient(s) (pharmaceutically acceptable excipients) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of formula I, and pharmaceutically acceptable excipients.

The term "optionally substituted" means "unsubstituted or substituted," and therefore, the generic structural formulas described herein encompass compounds containing the specified optional substituent as well as compounds that do not contain the optional substituent. For example, the phrase "aryl or heteroaryl each optionally substituted with 1 to 4 groups independently selected from Re" encompasses unsubstituted aryl or heteroaryl, and aryl or heteroaryl substituted with one, two, three or four substituents selected from Re; the same phrase can also be represented by the equivalent expression "Ar—($R^c$)0-4".

Each variable is independently defined each time it occurs within the generic structural formula definitions. For example, when there is more than one $R^c$ in "Ar—($R^c$)0-4" each $R^c$ is independently selected at each occurrence, and each $R^c$ can be the same or different from the other(s). In another example, the term —$OC(C_{1-3}$alkyl$)_2$- includes compounds in which the two alkyl substituents are of the same or different chain lengths.

For purposes of this specification, the following abbreviations have the indicated meanings Ac=acetyl; ADD=azodicarboxylic acid dipiperidide; DCM=dichloromethane; DMAP=4-(dimethylamino)pyridine; DMF=dimethylformamide; DMSO=dimethyl sulfoxide; EA=ethyl acetate; HATU=O-(7-azabenzotriazol-1-yl)-N,N,N',N'-tetramethyluronium hexa-fluorophosphate; HMDS=hexamethyldisilazide; NMP=N-methyl-2-pyrrolidinone; PPTS=pyridinium p-toluene sulfonate; TBAF=tetrabutylammonium fluoride; TBDMSi=t-butyldimethylsilyl; TFA=trifluoroacetic acid; THF=tetrahydrofuran; THP=tetrahydropyranyl; Ts=tosyl. Alkyl group abbreviations include: Me=methyl; Et=ethyl; n-Pr=normal propyl; i-Pr=isopropyl; c-Pr=cyclopropyl; n-Bu=normal butyl; i-Bu=isobutyl; c-Bu=cyclobutyl; s-Bu=secondary butyl; t-Bu=tertiary butyl.

Optical Isomers—Diastereomers—Geometric Isomers—Tautomers

Compounds of formula I contain one or more asymmetric centers and can thus occur as racemates and racemic mixtures, single enantiomers, diastereomeric mixtures and individual diastereomers. The present invention is meant to comprehend all such isomeric forms of the compounds of formula I.

Some of the compounds described herein contain olefinic double bonds, and unless specified otherwise, are meant to include both E and Z geometric isomers.

Some of the compounds described herein may exist with different points of attachment of hydrogen, referred to as tautomers. Such an example may be a ketone and its enol form known as keto-enol tautomers. The individual tautomers as well as mixture thereof are encompassed with compounds of formula I.

Compounds of the formula I may be separated into diastereoisomeric pairs of enantiomers by, for example, fractional crystallization from a suitable solvent, for example methanol or ethyl acetate or a mixture thereof. The pair of enantiomers thus obtained may be separated into individual stereoisomers by conventional means, for example by the use of an optically active acid as a resolving agent.

Alternatively, any enantiomer of a compound of the general formula I may be obtained by stereo specific synthesis using optically pure starting materials or reagents of known configuration.

Isotopes

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

Salts

The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that, unless otherwise specified, references to the compound of formula I, Ia, Ib, Ic, Id and Ie, and subsets thereof, embodiments thereof, as well as specific compounds are meant to also include pharmaceutically acceptable salts thereof.

Furthermore, some of the crystalline forms for compounds of the present invention may exist as polymorphs and as such all forms are intended to be included in the present invention. In addition, some of the compounds of the instant invention may form solvates with water (hydrates) or common organic solvents. Such solvates are encompassed within the scope of this invention.

Utilities

The ability of compounds of formula I to interact with prostaglandin receptors makes them useful for preventing or reversing undesirable symptoms caused by prostaglandins in a mammalian, especially human subject. This mimicking or antagonism of the actions of prostaglandins indicates that the compounds and pharmaceutical compositions thereof are useful to treat, prevent, or ameliorate in mammals and especially in humans: respiratory conditions, allergic conditions, pain, inflammatory conditions, mucus secretion disorders, bone disorders, sleep disorders, fertility disorders, blood coagulation disorders, trouble of the vision as well as immune and autoimmune diseases. In addition, such a compound may inhibit cellular neoplastic transformations and metastic tumor growth and hence can be used in the treatment of cancer. Compounds of formula I may also be of use in the treatment and/or prevention prostaglandin-mediated proliferation disorders such as may occur in diabetic retinopathy and tumor angiogenesis. Compounds of formula I may also inhibit prostanoid-induced smooth muscle contraction by antagonizing contractile prostanoids or mimicking relaxing prostanoids and hence may be used in the treatment of dysmenorrhea, premature labor and eosinophil related disorders. More particularly compounds of formula I are selective antagonists of prostaglandin D2 receptor, CRTH2.

Accordingly, another aspect of the invention provides a method of treating or preventing a prostaglandin mediated disease comprising administering to a mammalian patient in need of such treatment a compound of formula I in an amount which is effective for treating or preventing said prostaglandin mediated disease. Prostaglandin mediated diseases include, but are not limited to, allergic rhinitis, nasal congestion, rhinorrhea, perennial rhinitis, nasal inflammation, asthma including allergic asthma, chronic obstructive pulmonary diseases and other forms of lung inflammation; sleep disorders and sleep-wake cycle disorders; prostanoid-induced smooth muscle contraction associated with dysmenorrhea and premature labor; eosinophil related disorders; thrombosis; glaucoma and vision disorders; occlusive vascular diseases; congestive heart failure; diseases or conditions requiring a treatment of anti-coagulation such as post-injury or post surgery treatment; inflammation; gangrene;

Raynaud's disease; mucus secretion disorders including cytoprotection; pain and migraine; diseases requiring control of bone formation and resorption such as for example osteoporosis; shock; thermal regulation including fever; and immune disorders or conditions in which immunoregulation is desirable. More particularly the disease to be treated is one mediated by prostaglandin D2 such as nasal congestion, pulmonary congestion, and asthma including allergic asthma.

In one embodiment of the invention is a method of treating or preventing a prostaglandin mediated disease comprising administering to a mammalian patient in need of such treatment a compound of formula I in an amount which is effective for treating or preventing a prostaglandin mediated disease, wherein the prostaglandin mediated disease is nasal congestion, rhinitis including allergic and perennial rhinitis, and asthma including allergic asthma.

In another embodiment of the present invention is a method of treating or preventing a prostaglandin D2-mediated disease comprising administering to a mammalian patient in need of such treatment a compound of formula I in an amount which is effective for treating or preventing a prostaglandin D2 mediated disease wherein said prostaglandin D2 mediated disease is nasal congestion or asthma.

In another embodiment of the present invention is a method for the treatment of nasal congestion in a patient in need of such treatment which comprises administering to said patient a therapeutically effective amount of a compound of formula I.

In yet another embodiment of the present invention is a method for the treatment of asthma, including allergic asthma, in a patient in need of such treatment which comprises administering to said patient a therapeutically effective amount of a compound of formula I.

Dose Ranges

The magnitude of prophylactic or therapeutic dose of a compound of formula I will, of course, vary with the nature and the severity of the condition to be treated and with the particular compound of formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for the oral administration of humans may contain from 0.05 mg to 5 g of active agent compounded with an appropriate and convenient amount of carrier material which may vary from about 5 to about 99.95 percent of the total composition. Dosage unit forms will generally contain between from about 0.1 mg to about 0.4 g of an active ingredient, typically 0.5 mg, 1 mg, 2 mg, 5 mg, 10 mg, 25 mg, 50 mg, 100 mg, 200 mg, or 400 mg.

Pharmaceutical Compositions

Another aspect of the present invention provides pharmaceutical compositions comprising a compound of formula I with a pharmaceutically acceptable carrier. For the treatment of any of the prostanoid mediated diseases compounds of formula I may be administered orally, by inhalation spray, topically, parenterally or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleageous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing the compound of formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Combinations with Other Drugs

For the treatment and prevention of prostaglandin mediated diseases, compound of formula I may be co-administered with other therapeutic agents. Thus in another aspect the present invention provides pharmaceutical compositions for treating prostaglandin mediated diseases comprising a therapeutically effective amount of a compound of formula I and one or more other therapeutic agents. Suitable therapeutic agents for combination therapy with a compound of formula I include: (1) a DP receptor antagonist such as S-5751 and laropiprant; (2) a corticosteroid such as triamcinolone acetonide, budesonide, beclomethasone, fluticasone and mometasone; (3) a β-agonist such as salmeterol, formoterol, arformoterol, terbutaline, metaproterenol, albuterol and the like; (4) a leukotriene modifier, including a leukotriene receptor antagonist such as montelukast, zafirlukast, pranlukast, or a lipooxygenase inhibitor including 5-lipooxygenase inhibitors and FLAP (5-lipooxygenase activating protein) inhibitors such as zileuton; (5) an antihistamine such as bromopheniramine, chlorpheniramine, dexchlorpheniramine, triprolidine, clemastine, diphenhydramine, diphenylpyraline, tripelennamine, hydroxyzine, methdilazine, promethazine, trimeprazine, azatadine, cyproheptadine, antazoline, pheniramine pyrilamine, astemizole, terfenadine, loratadine, cetirizine, fexofenadine, descarboethoxyloratadine, and the like; (6) a decongestant including phenylephrine, phenylpropanolamine, pseudophedrine, oxymetazoline, ephinephrine, naphazoline, xylometazoline, propylhexedrine, or levo-desoxyephedrine; (7) an antiitussive including codeine, hydrocodone, caramiphen, carbetapentane, or dextramethorphan; (8) another prostaglandin ligand including prostaglandin F agonist such as latanoprost; misoprostol, enprostil, rioprostil, ornoprostol or rosaprostol; (9) a diuretic; (10) non-steroidal antiinflammatory agents (NSAIDs) such as propionic acid derivatives (alminoprofen, benoxaprofen, bucloxic acid, carprofen, fenbufen, fenoprofen, fluprofen, flurbiprofen, ibuprofen, indoprofen, ketoprofen, miroprofen, naproxen, oxaprozin, pirprofen, pranoprofen, suprofen, tiaprofenic acid, and tioxaprofen), acetic acid derivatives (indomethacin, acemetacin, alclofenac, clidanac, diclofenac, fenclofenac, fenclozic acid, fentiazac, furofenac, ibufenac, isoxepac, oxpinac, sulindac, tiopinac, tolmetin, zidometacin, and zomepirac), fenamic acid derivatives (flufenamic acid, meclofenamic acid, mefenamic acid, niflumic acid and tolfenamic acid), biphenylcarboxylic acid derivatives (diflunisal and flufenisal), oxicams (isoxicam, piroxicam, sudoxicam and tenoxican), salicylates (acetyl salicylic acid, sulfasalazine) and the pyrazolones (apazone, bezpiperylon, feprazone, mofebuta zone, oxyphenbutazone, phenylbutazone); (11) cyclooxygenase-2 (COX-2) inhibitors such as celecoxib and rofecoxib; (12) inhibitors of phosphodiesterase type IV (PDE-IV) e.g. Ariflo, roflumilast; (13) antagonists of the chemokine receptors, especially CCR-1, CCR-2, and CCR-3; (14) cholesterol lowering agents such as HMG-CoA reductase inhibitors (lovastatin, simvastatin and pravastatin, fluvastatin, atorvastatin, and other statins), sequestrants (cholestyramine and colestipol), nicotinic acid, fenofibric acid derivatives (gemfibrozil, clofibrat, fenofibrate and benzafibrate), and probucol; (15) anti-diabetic agents such as insulin, sulfonylureas, biguanides (metformin), α-glucosidase inhibitors (acarbose) and glitazones (troglitazone, pioglitazone, englitazone, rosiglitazone and the like); (16) preparations of interferon beta (interferon beta-1a, interferon beta-1b); (17) anticholinergic agents such as muscarinic antagonists (ipratropium bromide and tiotropium bromide), as well as selective muscarinic M3 antagonists; (18) steroids such as beclomethasone, methylprednisolone, betamethasone, prednisone, dexamethasone, and hydrocortisone; (19) triptans commonly used for the treatment of migraine such as sumitriptan and rizatriptan; (20) alendronate and other treatments for osteoporosis; (21) other compounds such as 5-aminosalicylic acid and prodrugs thereof, antimetabolites such as azathioprine and 6-mercaptopurine, cytotoxic cancer chemotherapeutic agents, bradykinin (BK2) antagonists such as FK-3657, TP receptor antagonists such as seratrodast, neurokinin antagonists (NK1/NK2), VLA-4 antagonists such as those described in U.S. Pat. No. 5,510,332, WO97/03094, WO97/02289, WO96/40781, WO96/22966, WO96/20216, WO96/01644, WO96/06108, WO95/15973 and WO96/31206. In addition, the invention encompasses a method of treating prostaglandin $D_2$ mediated diseases comprising: administration to a patient in need of such treatment a nontoxic therapeutically effective amount of a compound of formula I, optionally co-administered with one or more of such ingredients as listed immediately above.

Methods of Synthesis

Compounds of Formula I of the present invention can be prepared according to the synthetic routes outlined in Schemes 1 to 4 and by following the methods described herein.

Methods for the Preparation of Substituted Azaindoles

As shown in Scheme 1, azaindole 1-i in DCM treated with methyl chloro-oxoacetate 1-ii in the presence of aluminum chloride provides the ketoester 1-iii (See Tao Wang, J. Org. Chem. 2002, 67, 6226), which, when treated with triethylsilane in TFA, gives the ester compound 1.

Alternative methods for the preparation of azaindoles are shown in Scheme 1A. In one method, 2-amino-3-iodopyridine such as 1-iv is treated with an alkyne such as 1-v in the presence of a palladium catalyst to provide the azaindole 1a (see Feroze Ujjainwalla, Tetrahedron Letters 1998, 39, 5355 and Sang Sun Park, Tetrahedron Letters 1998, 39, 627). In another method, the acetylene 1-vi is lithiated with n-butyllithium followed by trapping with 4-bromobut-1-ene 1-vii to provide 1-viii. Aminoiodopyridine 1-ix is condensed on alkyne 1-viii to afford azaindole 1b using palladium as a catalyst as described above for azaindole 1a.

SCHEME 1

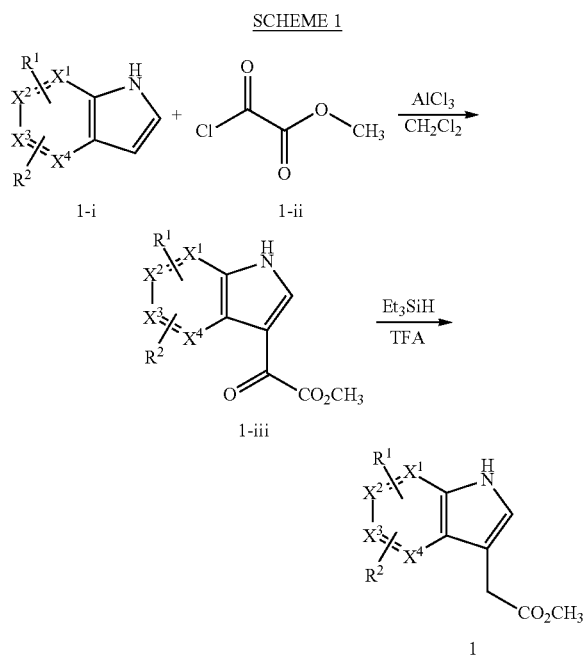

SCHEME 1A

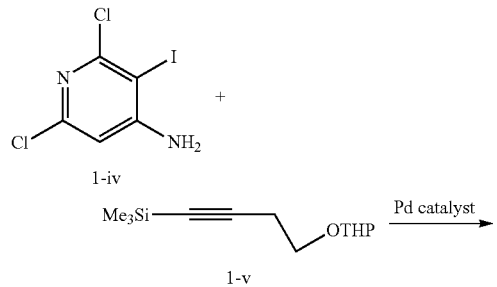

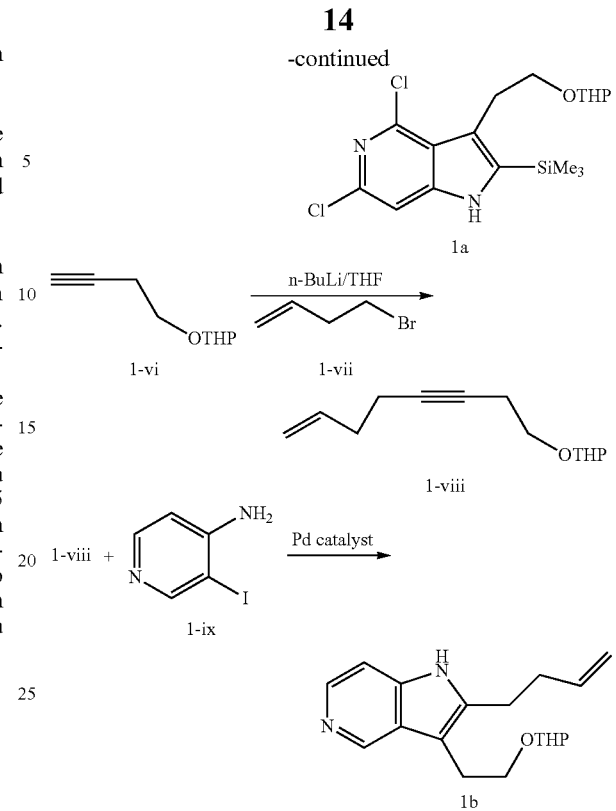

Methods for the Preparation of Aziridines

As shown in Scheme 2, aspartic acid dimethyl ester 2-i treated with sulfonyl chloride 2-ii in THF in the presence of triethylamine affords the sulfonyl amide diester 2-iii. Reduction of the diester 2-iii with e.g., sodium borohydride provides the diol 2-iv, which, under Mitsunobu conditions, provides the aziridine 2-v. The primary alcohol of 2-v can be protected with a silyl ether group to give protected aziridine 2.

Scheme 2A depicts another method for the preparation of protected aziridine. But-3-ene-1-ol 2-vi is converted to the silyl ether 2-vii by treatment with tert-butyldimethylsilyl chloride in the presence of imidazole. Compound 2-vii is then treated with chloramine-T in the presence of trimethylphenylammonium tribromide to provide the aziridine 2a.

SCHEME 2

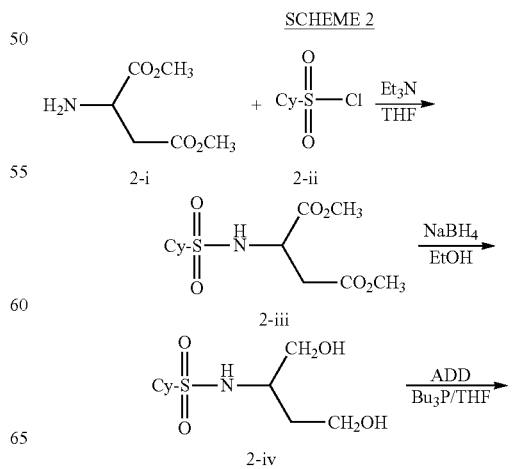

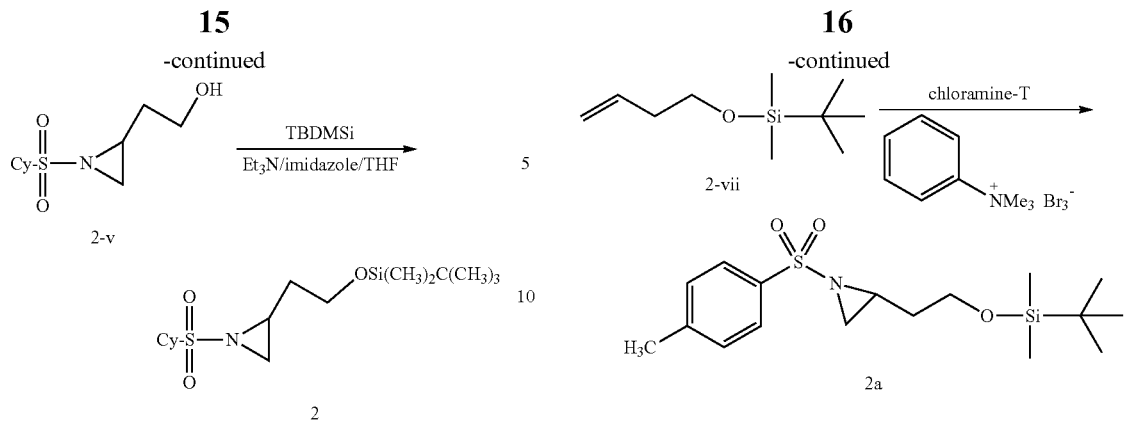

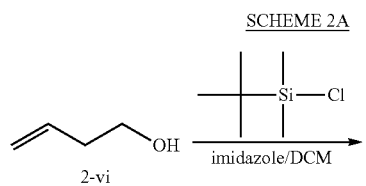

Method for the Preparation of Sulfonamide Intermediates 3

Scheme 3 shows the preparation of sulfonamide intermediates 3. The azaindole 1 is condensed on the aziridine 2 in the presence of sodium hydride to provide 3-i. The silyl group is removed with TBAF followed by oxidation with Dess-Martin reagent to afford the aldehyde 3-ii. The aldehyde 3-ii is heated in toluene in the presence PPTS to provide the corresponding cyclized compound, which is hydrogenated to give 3-iii. Compound 3-iii may be alkylated, for example with methyl iodide in the presence of sodium hydride, to provide 3-iv. The ester 3-iii or 3-iv is hydrolyzed with, for example, lithium hydroxide to give the free acid compound 3.

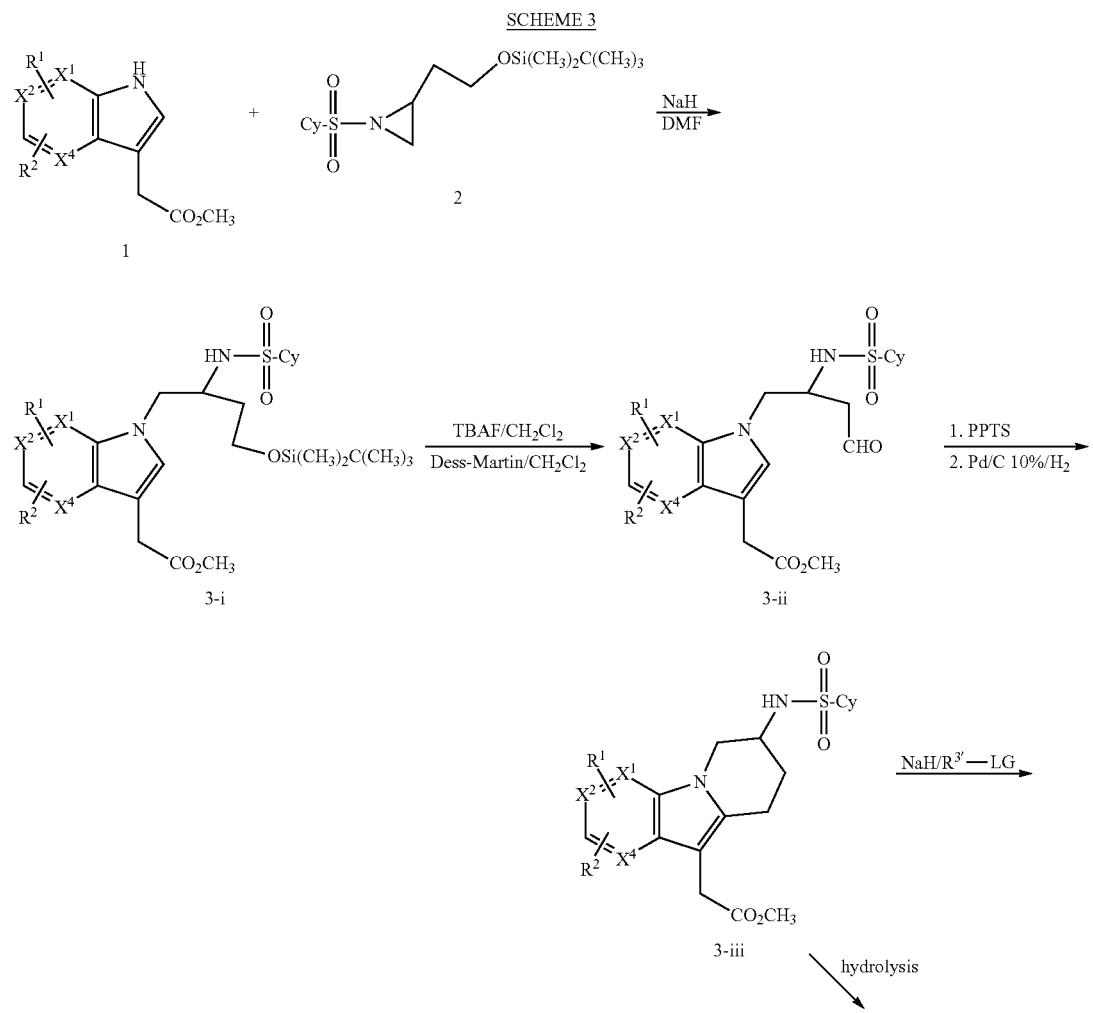

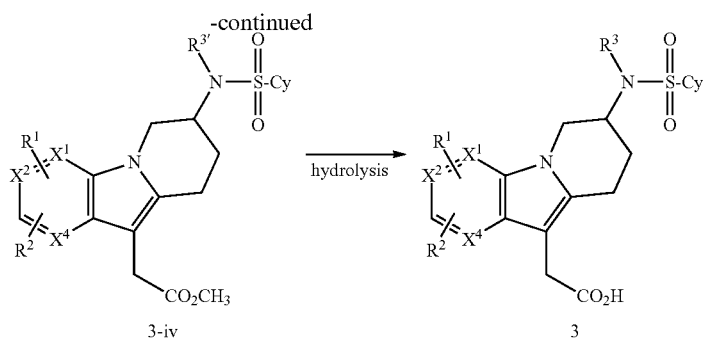

3-iv

R³' is a non-hydrogen group within the definition of R³
LG is a leaving group such as Cl Scheme 3A shows the preparation of compounds of formula 3a. Using conditions described in Scheme 3, the azaindole 3-v can be converted to the aldehyde 3-vi and subsequently to compound 3-vii, which in turn can be converted to compound 3-viii using standard conditions (For NaClO$_2$ oxidation see: JACS 1984, 106, 7217). The double bond of compound 3-viii can be hydrogenated, followed by hydrolysis of the ester to give a compound of formula 3a.

SCHEME 3A

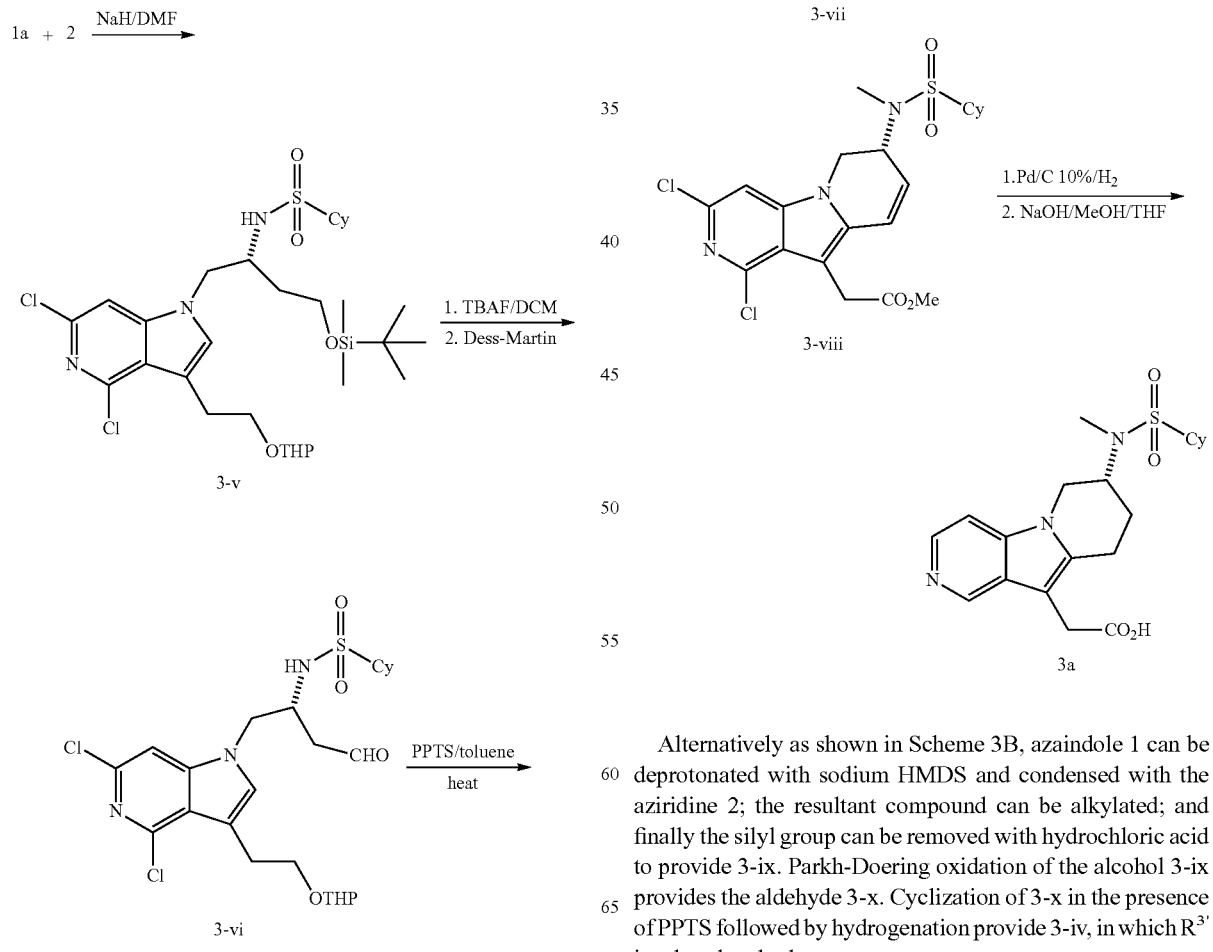

Alternatively as shown in Scheme 3B, azaindole 1 can be deprotonated with sodium HMDS and condensed with the aziridine 2; the resultant compound can be alkylated; and finally the silyl group can be removed with hydrochloric acid to provide 3-ix. Parkh-Doering oxidation of the alcohol 3-ix provides the aldehyde 3-x. Cyclization of 3-x in the presence of PPTS followed by hydrogenation provide 3-iv, in which R³' is other than hydrogen.

SCHEME 3B

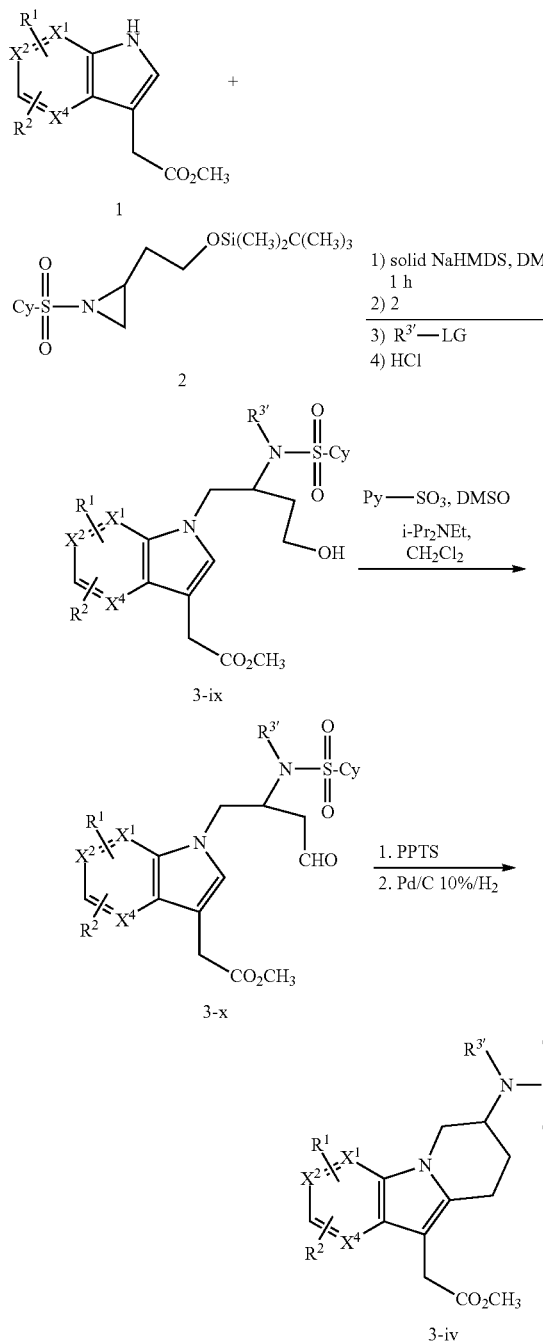

SCHEME 4

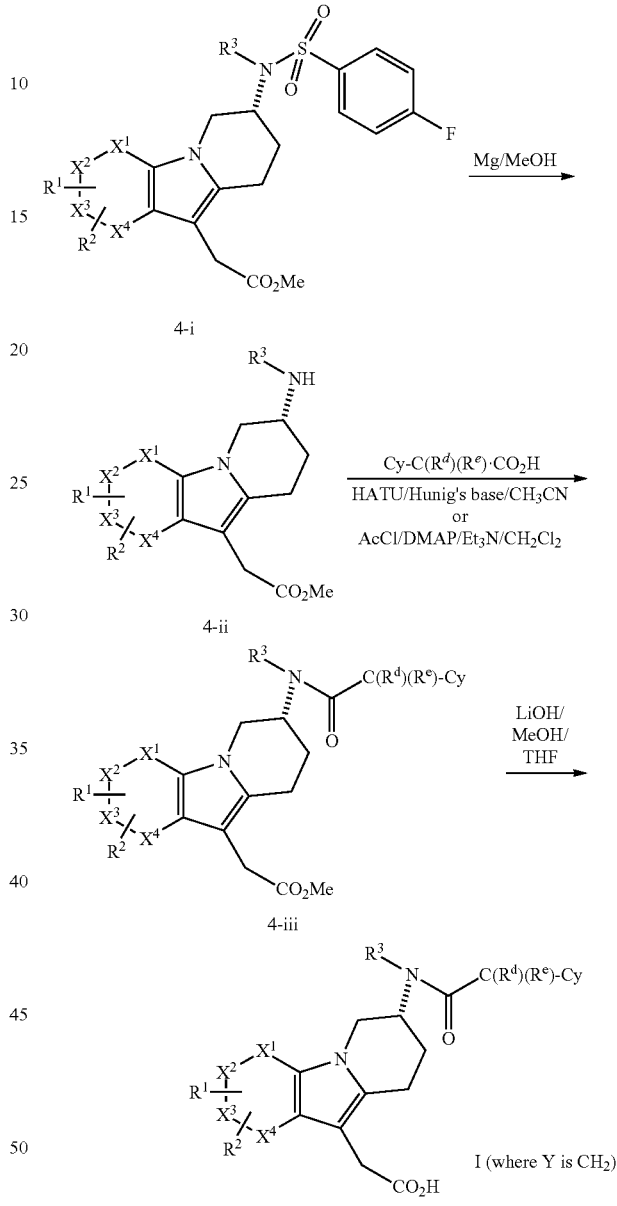

Method for the Preparation of Compounds of Formula I

As shown in Scheme 4, sulfonamide 4-i when treated with magnesium in methanol (See Monika Fitz Tetrahedron Asymmetry 2005, 16, 3690 for examples of sulfonamide cleavage) provides the amine 4-ii. The amine 4-ii can be converted to the amide 4-iii using HATU as coupling reagent with an acid or acylated with an acyl chloride. The ester 4-iii can then be hydrolyzed to provide the free acid of formula I. Amines 4-ii in which $R^3$ is hydrogen can be alkylated by reductive amination; for example, treatment of 4-ii ($R^3$=H) with benzlaldehyde and $NaBH(OAc)_3$ provides the corresponding benzylamine. Amides 4-iii in which $R^3$ is hydrogen can be alkylated as described in Scheme 3 for the sulfonamide series.

Compounds of formula I in which Y is other than methylene may be prepared according to the general procedures outlined in WO2007019675, the relevant portions are hereby incorporated by reference.

Compounds of formula I can be prepared according to the procedures described in the Schemes and Examples herein, using appropriate materials and are further exemplified by the following specific examples. The compounds exemplified are representative of the invention, and are not to be construed as limiting the scope of the invention in any manner. The examples further illustrate details for the preparation of the compounds of the present invention. Those skilled in the art will readily understand that known variations of protecting groups, of reagents, as well as of the conditions and processes of the following preparative procedures, can be used to prepare these compounds. It is also understood that whenever a chemical reagent is not commercially available, such a chemical reagent can be readily prepared by those skilled in the art by either following or adapting known methods described in the literature. All temperatures are degrees Celsius unless otherwise noted. Mass spectra (MS) were measured either by electrospray ion-mass spectroscopy (ESMS) or by atmospheric pressure chemical ionization mass spectroscopy (APCI).

PREPARATION OF INTERMEDIATE I-1

Methyl {(8R)-8-[[(4-fluorophenyl)sulfonyl](methyl)amino]-6,7,8,9-tetrahydropyrido[3,2-b]-indolizin-5-yl}acetate

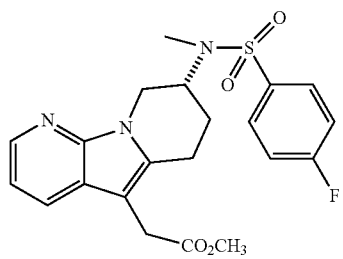

I-1

Step 1: Methyl oxo(1H-pyrrolo[2,3-b]pyridin-3-yl)acetate

To a suspension of aluminum chloride (56.4 g, 423 mmol, 5 equiv.) in DCM (50 mL) was added 7-azaindole (10.0 g, 85 mmol). After 1 h at room temperature the resulting mixture was cooled to 0° C. and methyl chlorooxoacetate (51.9 g, 423 mmol, 5 equiv.) was added dropwise. After a period of 18 h at room temperature the reaction mixture was cooled to 0° C. and methanol (300 mL) was added. After a period of 0.5 h at room temperature, the solvents were evaporated. DCM (500 mL) and saturated $NaHCO_3$ (600 mL) were added. The organic layer was separated and the water extracted with DCM (250 mL). The organic phases were combined and stirred for 18 h with a solution of potassium sodium tartrate (166 g in 500 mL of water). The organic phase was separated, dried over sodium sulfate, filtered and evaporated under reduced pressure. The residue was purified by flash chromatography with 50% ethyl acetate in hexane to provide 13 g of the title compound.

Step 2: Methyl 1H-pyrrolo[2,3-b]pyridin-3-ylacetate

To a mixture of triethylsilane (9.95 g, 85.78 mmol) in TFA (25 mL) was added portionwise methyl oxo(1H-pyrrolo[2,3-b]pyridin-3-yl)acetate (5.0 g, 24.48 mmol). After a period of 18 h at 50° C., the solvent was evaporated and saturated $NaHCO_3$ was added followed by DCM. The organic phase was separated, dried over magnesium sulfate, filtered and evaporated under reduced pressure. The residue was purified by combiflash with 10% ethyl acetate in hexane to 100% ethyl acetate to provide 3.5 g of the title compound.

Step 3: D-Aspartic acid dimethyl ester hydrochloride

To a suspension of D-aspartic acid (25 g, 188 mmol) in methanol (250 mL) at 0° C. was added dropwise over 30 min. thionyl chloride (15.1 mL, 207 mmol). After a period of 24 h at room temperature, the solvent was removed under reduced pressure and the residue was co-evaporated two times with methanol. To the residue was added THF and co-evaporated two times with THF. The title compound was suspended in 400 mL of THF and used as such for the next step.

Step 4: Dimethyl N-[(4-fluorophenyl)sulfonyl]-D-aspartate

To a suspension of D-aspartic acid dimethyl ester hydrochloride (36.0 g, 182 mmol) in THF (360 mL) was added 4-fluorobenzenesulfonyl chloride (39.0 g, 200 mmol, 1.1 equiv.). To the previous mixture at 0° C. was added dropwise triethylamine (60.8 g, 601 mmol, 3.3 equiv.). After a period of 18 h at room temperature, the reaction mixture was filtered and the solid washed with methyl tert-butyl ether (30 mL). The filtrate was evaporated followed by the addition of methyl tert-butyl ether (300 mL). To the resulting mixture was added 100 mL of HCl 1 M. The organic phase was separated and sequentially washed with water, half-saturated sodium bicarbonate, HCl 0.5 M and half-saturated sodium chloride. The organic phase was dried over magnesium sulfate, filtered and evaporated under reduced pressure to give 50 g of the title compound as an oil.

Step 5: 4-Fluoro-N-[(1R)-3-hydroxy-1-(hydroxymethyl)propyl]benzenesulfonamide To a suspension of dimethyl N-[(4-fluorophenyl)sulfonyl]-D-aspartate (50 g, 157 mmol) in ethanol (500 mL) at 0° C. was added portionwise sodium borohydride (29.6 g, 783 mmol, 5 equiv.) over 2.5 h. After a period of 18 h at room temperature the reaction was quenched by the addition of saturated sodium chloride (500 mL). The resulting mixture was filtered and the filtrate was concentrated under reduced pressure to a volume of about 500 mL. To this mixture was added concentrated HCl until pH 3-4 and the mixture was saturated with sodium chloride. The aqueous phase was extracted with ethyl acetate (5×200 mL). The solid obtained from the sodium chloride quench was dissolved in 1 M HCl and extracted with ethyl acetate after the addition of sodium chloride. The organic phases were combined, washed with saturated sodium chloride dried over sodium sulfate, filtered and evaporated under reduced pressure. The mixture was purified by flash chromatography with ethyl acetate to give 35 g of the title compound.

Step 6: 2-{(2R)-1-[(4-Fluorophenyl)sulfonyl]aziridin-2-yl}ethanol

To 4-fluoro-N-[(1R)-3-hydroxy-1-(hydroxymethyl)propyl]benzenesulfonamide (35.0 g, 133 mmol) in THF (700 mL) was added 1,1'-(azodicarbonyl)dipepiridine (35.0 g, 139 mmol, 1.04 equiv.) followed by tributylphosphine (28.7 g, 142 mmol, 1.07 equiv.) over 10 min. After a period of 2 h, the reaction mixture was filtered and the solid washed with methyl tert-butyl ether (100 mL). Water (200 mL) was added to the filtrate and the organic phase was separated which in turn was washed with 100 mL of 3% hydrogen peroxide. The organic phase was then washed with water and half-saturated sodium chloride. The organic phase was collected, dried over magnesium sulfate, filtered and evaporated under reduced pressure. The residue was treated with methyl tert-butyl ether and the mixture filtered. The filtrate was evaporated and purified by flash chromatography with 50% ethyl acetate to 70% ethyl acetate in hexane to provide 31 g of the title compound.

Step 7: (2R)-2-(2-{[tert-Butyl(dimethyl)silyl]oxy}ethyl)-1-[(4-fluorophenyl)sulfonyl]-aziridine To a solution of 2-{(2R)-1-[(4-fluorophenypsulfonyl]aziridin-2-yl}ethanol (17.5 g, 71.3 mmol) in THF (175 mL) were added tert-butyldimethylsilyl chloride (11.8 g, 78 mmol, 1.1 equiv.) followed by imidazole (10.7 g, 157 mmol, 2.2 equiv.). After a period of 2 h, the solid was filtered and methyl tert-butyl ether (75 mL) was added. To the filtrate was added water (100 mL) and the organic phase separated. The organic phase was washed with half-saturated sodium chloride, saturated sodium chloride, dried over magnesium sulfate, filtered and evaporated under reduced pressure. The residue was purified by flash chromatography with 10% ethyl acetate in hexane to give 20 g of the title compound.

Step 8: Methyl[1-((2R)-4-{[tert-butyl(dimethyl)silyl]oxy}-2-{[(4-fluorophenyl)sulfonyl]-amino}butyl)-1H-pyrrolo[2,3-b]pyridin-3-yl]acetate To a cooled solution at 0° C. of methyl 1H-pyrrolo[2,3-b]pyridin-3-ylacetate (1.1 g, 5.8 mmol) in DMF (12 mL) was added 60% NaH in oil (0.26 g, 6.4 mmol, 1.1 equiv.). After a period of 10 min at room temperature, the reaction mixture was cooled to 0° C. and a DMF solution (12 mL) of (2R)-2-(2-{[tert-butyl(dimethyl)silyl]oxy}ethyl)-1-[(4-fluorophenyl)-sulfonyl]aziridine (2.0 g, 5.8 mmol) was added. The reaction was aged 0.5 h at room temperature and poured over saturated ammonium chloride and ethyl acetate. The organic phase was separated, dried over sodium sulfate, filtered and evaporated under reduced pressure. The residue was purified by combiflash (hexane to 50% ethyl acetate in hexane) to provide 1.2 g of the title compound.

Step 9: Methyl [1-((2R)-2-{[(4-fluorophenyl)sulfonyl]amino}-4-hydroxybutyl)-1H-pyrrolo[2,3-b]pyridin-3-yl]acetate To a solution of methyl [1-((2R)-4-{[tert-butyl(dimethyl)silyl]oxy}-2-{[(4-fluorophenyl)sulfonyl]amino}butyl)-1H-pyrrolo[2,3-b]pyridin-3-yl]acetate (1.2 g, 2.2 mmol) in dichloromethane (40 mL) was added 1 M TBAF (4.8 mL, 2.2 equiv.). After a period of 0.5 h the reaction mixture was quenched with 25% aqueous ammonium acetate, the organic phase was separated, dried over sodium sulfate, filtered and evaporated under reduced pressure. The residue was purified on combiflash (20% ethyl acetate in hexane to 100% ethyl acetate) to provide 849 mg of the title compound.

Step 10: Methyl [1-((2R)-2-{[(4-fluorophenyl)sulfonyl]amino}-4-oxobutyl)-1H-pyrrolo[2,3-b]pyridin-3-yl]acetate To a solution of methyl [1-((2R)-2-{[(4-fluorophenyl)sulfonyl]amino}-4-hydroxybutyl)-1H-pyrrolo[2,3-b]pyridin-3-yl]acetate (0.89 g, 1.9 mmol) in dichloromethane (16 mL) was added Dess-Martin reagent (0.99 g, 2.3 mmol, 1.2 equiv.). After a period of 45 min. the reaction mixture was purified directly by combiflash (20% ethyl acetate in hexane to 100% ethyl acetate) to give 697 mg of the title compound.

Step 11: Methyl ((8R)-8-{[(4-fluorophenyl)sulfonyl]amino}-8,9-dihydropyrido[3,2-b]-indolizin-5-yl)acetate To a mixture of methyl [1-((2R)-2-{[(4-fluorophenyl)sulfonyl]amino}-4-oxobutyl)-1H-pyrrolo[2,3-b]pyridin-3-yl]acetate (0.69 g, 1.6 mmol) in toluene (50 mL) was added PPTS (0.41 g, 1.6 mmol, 1.2 equiv.). After a period of 10 h at 90° C., the reaction mixture was quenched with saturated sodium bicarbonate and extracted with ethyl acetate. The organic phase was separated, dried over sodium sulfate, filtered and evaporated under reduced pressure. The residue was purified by combiflash (10% ethyl acetate in hexane to 100% ethyl acetate) to give 469 mg of the title compound.

Step 12: Methyl ((8R)-8-{[(4-fluorophenyl)sulfonyl]amino}-6,7,8,9-tetrahydropyrido-[3,2-b]indolizin-5-yl)acetate To a solution of methyl ((8R)-8-{[(4-fluorophenyl)sulfonyl]amino}-8,9-dihydropyrido[3,2-b]indolizin-5-yl)acetate (0.46 g, 1.1 mmol) in ethyl acetate (20 mL) was added under nitrogen Pd—C 10% (0.02 g, 0.19 mmol, 0.17 equiv.). After a period of 1 h under 1 atmosphere of $H_2$, DCM was added to the reaction mixture which in turn was filtered over a micro filter and the solvents were evaporated to afford 464 mg of the title compound.

Step 13: Methyl {(8R)-8-[[(4-fluorophenyl)sulfonyl](methyl)amino]-6,7,8,9-tetrahydro-pyrido[3,2-b]indolizin-5-yl}acetate To a solution of methyl ((8R)-8-{[(4-fluorophenyl)sulfonyl]amino}-6,7,8,9-tetrahydropyrido[3,2-b]indolizin-5-yl)acetate (0.46 g, 1.1 mmol) in DMF (5.5 mL) was added at 0° C. under nitrogen 60% NaH in oil (0.04 g, 1.2 mmol, 1.1 equiv.). After a period of 10 min., methyl iodide (0.076 mL, 1.2 mmol, 1.1 equiv.) was added and the reaction mixture aged 1 h at room temperature. The reaction mixture was poured over 25% aqueous ammonium acetate solution and ethyl acetate. The organic phase was separated, dried over sodium sulfate, filtered and evaporated under reduced pressure. The residue was purified by combiflash (hexane to 100% ethyl acetate) to provide 420 mg of the title compound.

Alternative Route

Step 1: Methyl {1-[(2R)-2-{[(4-fluorophenyl)sulfonyl](methyl)amino}-4-hydroxybutyl]-1H-pyrrolo[2,3-b]pyridin-3-yl}acetate To a stirred solution of NaHMDS (177.22 g, 966 mmol) in DMF (600 ml) at −10° C. was added a solution of methyl 1H-pyrrolo[2,3-b]pyridin-3-ylacetate (197.98 g, 969 mmol) in DMF (1000 ml) over 15 min., and stirring continue at that temperature for 2 hours. To the anion was added a solution of (2R)-2-(2-{[tert-butyl(dimethyl)silyl]oxy}ethyl)-1-[(4-fluoro-phenyl)sulfonyl]aziridine (288 g, 801 mmol) in DMF (1000 ml) over 1 hour. The reaction mixture was stirred for 1 hour at −10° C. Iodomethane (125.0 ml, 1999 mmol) was added at −10° C. and the reaction was stirred for 1.5 hour.

Another aliquot of iodomethane (20 mL) was then added and the reaction was stirred for 30 more minutes. 3N HCl (1800 ml, 5400 mmol) was added slowly at −10° C. and the reaction was stirred for an additional hour. The reaction was quenched by pouring into saturated sodium bicarbonate solution (4 L) and ethyl acetate (4 L). The pH was still acidic so additional solid sodium bicarbonate was added. The layers were separated and the organic layer washed with ½ brine (1×4 L) and (1×2 L).

Step 2: Methyl {1-[(2R)-2-{[(4-fluorophenyl)sulfonyl](methyl)amino}-4-oxobutyl]-1H-pyrrolo[2,3-b]pyridin-3-yl}acetate To DMSO (1 L, 1.41E+04 mmol) at room temperature was added pyridine sulfur trioxide (202.08 g, 1270 mmol) and the reaction mixture was stirred for 30 min at room temperature (solution A). In another flask, to a stirred solution of methyl {1-[(2R)-2-{[(4-fluorophenyl)sulfonyl](methyl)amino}-4-hydroxybutyl]-1H-pyrrolo[2,3-b]pyridin-3-yl}acetate (273 g, 589 mmol) and Hunig's base (0.425 L, 2433 mmol) in dichloromethane (4 L) at −10° C. was added solution A dropwise over 30 min. The reaction was stirred at −10° C. for 1 h. then quenched by adding ½ saturated brine (4 L); the aqueous layer was neutralized with solid sodium bicarbonate. The layers were then separated and the organic layer was washed with ½ saturated brine (4 L), dried over sodium sulfate, filtered and evaporated under reduced pressure. The residue was purified by flash chromatography with ethyl acetate to provide the title compound.

Step 3: Methyl ((8R)-8-{[(4-fluorophenyl)sulfonyl](methyl)amino}-8,9-dihydro-pyrido[3,2-b]indolizin-5-yl)acetate To a mixture of methyl [1-((2R)-2-{[(4-fluorophenyl)sulfonyl](methyl)amino}-4-oxobutyl]-1H-pyrrolo[2,3-b]pyridin-3-yl]acetate (272 g, 589 mmol) in ethyl acetate (2.5 L) was added PPTS (326.33 g, 1299 mmol). After a period of 4 days at 65° C., the reaction mixture was quenched with saturated sodium bicarbonate and extracted with ethyl acetate. The organic phase was separated, washed with brine, dried over sodium sulfate, filtered and evaporated under reduced pressure. The residue was purified by combiflash (10% ethyl acetate in hexane to 100% ethyl acetate) to give the title compound.

Step 4: Methyl ((8R)-8-{[(4-fluorophenyl)sulfonyl](methyl)amino}-6,7,8,9-tetrahydro-pyrido[3,2-b]indolizin-5-yl)acetate To a solution of methyl ((8R)-8-{[(4-fluorophenyl)sulfonyl](methyl)amino}-8,9-dihydropyrido[3,2-b]indolizin-5-yl)acetate (105 g, 237 mmol) in ethyl acetate (500 mL) was added under nitrogen Pd—C 10% (5.04 g, 47.4 mmol). After a period of 48 h under 1 atmosphere of $H_2$, the reaction was transferred to the Parr and allowed to sit at 10 psi $H_2$ for 1 h. The reaction was filtered over solka-flok. Another batch of Pd—C 10% (5.45 g) was added and the reaction was allowed to stir under 1 atmosphere of $H_2$ overnight. The reaction mixture was then filtered over solka-flok and rinsed with ethyl acetate. After the solvent was removed under reduced pressure, the title compound was obtained.

EXAMPLE 1

((8R)-8-{Methyl[(2R)-2-(4-fluorophenyl)propanoyl]amino}-6,7,8,9-tetrahydropyrido[3,2-b]-indolizin-5-yl)acetic acid (isomer A) and ((8R)-8-{Methyl[(2S)-2-(4-fluorophenyl)propanoyl]-amino}-6,7,8,9-tetrahydropyrido[3,2-b]indolizin-5-yl)acetic acid (isomer B)

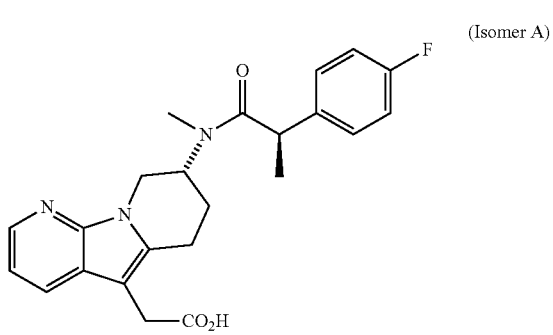

(Isomer A)

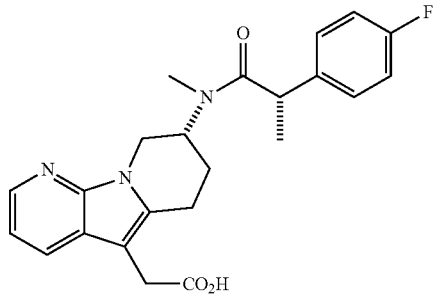

(Isomer B)

Step 1: Methyl[(8R)-8-(methylamino)-6,7,8,9-tetrahydropyrido[3,2-b]indolizin-5-yl]-acetate To a degassed solution of Intermediate I-1 (3.70 g, 8.58 mmol) in MeOH (110 mL) was added ribbon magnesium (2.08 g, 86.0 mmol). The mixture was heated at 50° C. until total consumption of magnesium. The reaction was cooled to room temperature and excess of DCM and methyl acetate were added. The mixture was evaporated followed by the addition of DCM and methyl acetate. The mixture was filtered and the filtrate was evaporated. The residue was dissolved in DCM and purified by combiflash (DCM to 30% MeOH in DCM) to provide 1.9 g of the title compound.

Step 2: Methyl{(8R)-8-[[(2R)-2-(4-fluorophenyl)propanoyl](methyl)amino]-6,7,8,9-tetrahydropyrido[3,2-b]indolizin-5-yl}acetate (isomer A) and Methyl{(8R)-8-[[(2S)-2-(4-fluorophenyl(propanoyl]methyl)amino]-6,7,8,9-tetrahydropyrido[3,2-b]indolizin-5-yl}acetate (isomer B)

To a DMF (1 mL) solution of 2-(4-fluorophenyl)propanoic acid (0.10 g, 0.62 mmol), HATU (0.24 g, 0.62 mmol) and N,N-diisopropyethylamine was added methyl [(8R)-8-(methylamino)-6,7,8,9-tetrahydropyrido[3,2-b]indolizin-5-yl]acetate (0.11 g, 0.42 mmol). After a period of 16 h at room temperature, aqueous ammonium chloride was added followed by extraction of the aqueous phase with isopropylacetate. The organic phase was extracted with brine, dried over MgSO₄ and evaporated under reduced pressure. The residue was purified by combiflash (hexane to ethyl acetate) to give 0.16 g of material. The mixture of diastereomers was separated by chiral HPLC (Chiralpak AD 50×500 mm, MeOH 40%/EtOH 40%/Et₃N 0.25% in hexane). The fast eluting isomer A methyl ester (0.067 g) corresponding to methyl ((8R)-8-{methyl(2R)-2-(4-phenyl)propanoyl]amino}-6,7,8, 9-tetrahydropyrido[3,2-b]indolizin-5-yl)-acetate acetate and the slow eluting isomer B methyl ester to methyl ((8R)-8-{methyl[(2S)-2-(4-phenyl)-propanoyl]amino}-6,7,8,9-tetrahydropyrido[3,2-b]indolizin-5-yl)acetate (0.067 g).

Step 3: {(8R)-8-[[(2R)-2-(4-Fluorophenyl)propanoyl](methyl)amino]-6,7,8,9-tetrahydro-pyrido[3,2-b]indolizin-5-yl}acetic acid (isomer A) and {(8R)-8-8-[[(2S)-2-(4-fluorophenyl)propanoyl](methyl)amino]-6,7,8,9-tetrahydropyrido[3,2-b]indolizin-5-yl}acetic acid (isomer B)

To a solution of methyl {(8R)-8-[[(2R)-2-(4-fluorophenyl)propanoyl](methyl) amino]-6,7,8,9-tetrahydropyrido[3,2-b]indolizin-5-yl}acetate (0.067 g, 0.16 mmol) in THF (3 mL) and MeOH (1.5 mL) was added 2 M NaOH (1.6 mL) After a period of 1 h at room temperature, 1 M HCl was added to the reaction mixture followed by DCM. The organic phase was collected with a phase separator to provide 0.045 g of the isomer A. m/z 410 (M+H)⁺. Using the same protocol the isomer B was prepared from methyl {(8R)-8-[[(2S)-2-(4-fluorophenyl)-propanoyl](methyl)amino]-6,7,8,9-tetrahydropyrido[3,2-b]indolizin-5-yl}acetate. Alternatively, LiOH in CH₃CN was also used for the hydrolysis of the ester. m/z 410.

Alternatively isomers A and B methyl esters could be prepared, respectively, from (2R)-2-(4-fluorophenyl)proponoic acid and (2S)-2-(4-fluorophenyl)proponoic acid (see J. Med. Chem, 2007, 3870 for the synthesis of both acids) as follow:

To a DMF (96 mL) solution of (2R)-2-(4-fluorophenyl) propanoic acid (1.96 g, 11.7 mmol) was added HATU (6.68 g, 17.5 mmol). To the resulting mixture at 0° C., was added 2,6-lutidine (1.29 g, 12.9 mmol). After a period of 15 min at 0° C., a solution (30 mL) of methyl [(8R)-8-(methylamino)-6,7,8,9-tetrahydropyrido[3,2-b]indolizin-5-yl]acetate (3.20 g, 11.7 mmol) and 2,6-lutidine (2.48 g, 23.2 mmol) in DMF was added to the previous mixture. After a period of 30 min at 0° C., the reaction was warmed to room temperature. The reaction was then quenched by the addition of water and ethyl acetate. The organic phase was separated, dried over Na₂SO₄, filtered and evaporated under reduced pressure. The resulting mixture was purified by combiflash (40% to 100% ethyl acetate in hexane) to provide 3.2 g of the isomer A methyl ester. The ester was then purified by chiral HPLC (Chiralpak AD 50×500 mm, MeOH 40%/EtOH 40%/Et₃N 0.25% in hexane) to give the isomer A methyl ester >99% de.

To the isomer A methyl ester (3.70 g, 8.74 mmol) in acetonitrile (30 mL) was added 2 M LiOH (6.55 mL, 13.1 mmol). After completion of the reaction, saturated aqueous NH₄Cl was added followed by DCM. The organic phase was separated and the aqueous phase extracted with ethyl acetate and 2-methyltetrahydrofuran. The organic phases were combined, dried over Na₂SO₄, filtered and evaporated under reduced pressure. The isomer A was dissolved in hot ethyl acetate followed by the addition of hexane at room temperature. After a period of 18 h, the resulting solid was filtered to provide 2.98 g of the title compound.

EXAMPLE 2

{(8R)-8-[[2-(4-fluorophenyl)-3-methylbutanoyl] (methyl)amino]-6,7,8,9-tetrahydropyrido[3,2-b]-indolizin-5-yl}acetic acid

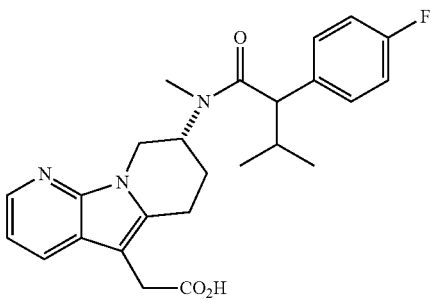 [SMILES: CC(C)C(C(=O)N(C)[C@@H]1CCc2c(CC(=O)O)c3cccnc3n2C1)c1ccc(F)cc1]

The title compound was prepared as described in example 1 using 2-(4-fluorophenyl)-3-methylbutanoic acid for the coupling reaction. The mixture of diastereomers was separated on chiral HPLC (AD column 10% EtOH/10% MeOH/ 0.25% HCOOH in hexane). More mobile isomer: m/z 438 (M+1)⁺. Less mobile isomer: m/z 438 (M+1)⁺.

EXAMPLE 3

{(8R)-8-[(diphenylacetyl)(methyl)amino]-6,7,8,9-tetrahydropyrido[3,2-b]indolizin-5-yl}acetic acid

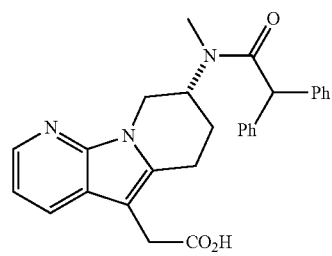 [SMILES: CN(C(=O)C(c1ccccc1)c1ccccc1)[C@@H]1CCc2c(CC(=O)O)c3cccnc3n2C1]

The title compound was prepared as described in example 1 using diphenylacetic acid for the coupling reaction. m/z (453 M+1)⁺.

EXAMPLE 4

{(8R)-8-[[2-(4-fluorophenyl)-2-methylpropanoyl] (methyl)amino]-6,7,8,9-tetrahydropyrido[3,2-b]indolizin-5-yl}acetic acid

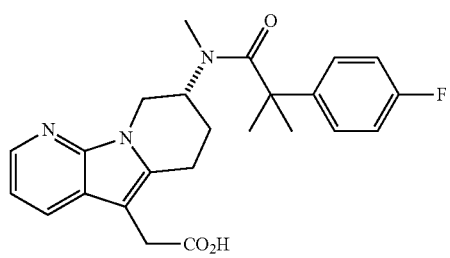 [SMILES: CN(C(=O)C(C)(C)c1ccc(F)cc1)[C@@H]1CCc2c(CC(=O)O)c3cccnc3n2C1]

The title compound was prepared as described in example 1 using 2-(4-fluorophenyl)-2-methylpropanoic acid for the coupling reaction. m/z (423 M+1)+.

EXAMPLE 5

{(8R)-8-[{[4-(4-fluorophenyl)tetrahydro-2H-pyran-4-yl]carbonyl}(methyl)amino]-6,7,8,9-tetrahydropyrido[3,2-b]indolizin-5-yl}acetic acid

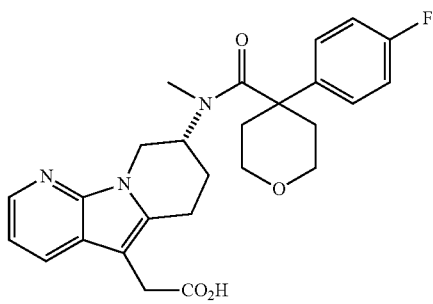 [SMILES: CN(C(=O)C1(c2ccc(F)cc2)CCOCC1)[C@@H]1CCc2c(CC(=O)O)c3cccnc3n2C1]

The title compound was prepared as described in example 1 using 4-(4-fluorophenyl)tetrahydro-2H-pyran-4-carboxylic acid for the coupling reaction. m/z (465 M+1)+.

EXAMPLE 6

{(8R)-8-[{[1-(4-fluorophenyl)-2,2-dimethylcyclopropyl]carbonyl}(methyl)amino]-6,7,8,9-tetrahydropyrido[3,2-b]indolizin-5-yl}acetic acid

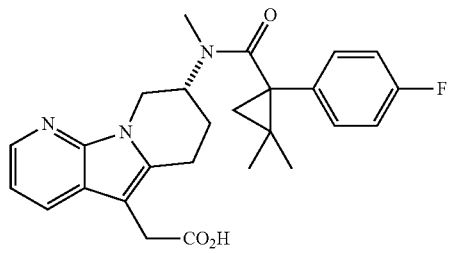 [SMILES: CN(C(=O)C1(c2ccc(F)cc2)CC1(C)C)[C@@H]1CCc2c(CC(=O)O)c3cccnc3n2C1]

The title compound was prepared as described in example 1 using 1-(4-fluorophenyl)-2,2-dimethylcyclopropanecarboxylic acid for the coupling reaction. m/z (449 M+1)+.

EXAMPLE 7

{(8R)-8-[{[1-(4-fluorophenyl)cyclobutyl]carbonyl}(methyl)amino]-6,7,8,9-tetrahydropyrido[3,2-b]indolizin-5-yl}acetic acid

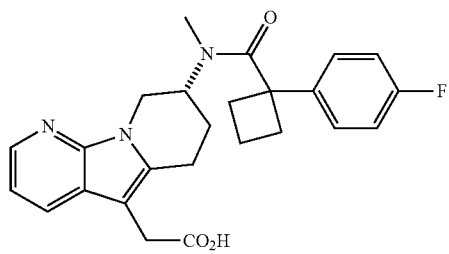 [SMILES: CN(C(=O)C1(c2ccc(F)cc2)CCC1)[C@@H]1CCc2c(CC(=O)O)c3cccnc3n2C1]

The title compound was prepared as described in example 1 using 1-(4-fluorophenyl)cyclobutanecarboxylic acid for the coupling reaction. m/z (435 M+1)+.

EXAMPLE 8

{(8R)-8-[{[1-(4-fluorophenyl)cyclopentyl]carbonyl}(methyl)amino]-6,7,8,9-tetrahydro-pyrido[3,2-b]indolizin-5-yl}acetic acid

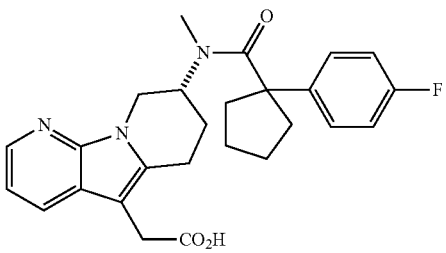 [SMILES: CN(C(=O)C1(c2ccc(F)cc2)CCCC1)[C@@H]1CCc2c(CC(=O)O)c3cccnc3n2C1]

The title compound was prepared as described in example 1 using 1-(4-fluorophenyl)cyclopentanecarboxylic acid for the coupling reaction. m/z (449 M+1)+.

BIOLOGICAL ASSAYS

Compounds of the present invention may be evaluated as CRTH2 antagonists using one or more of the following assays.

Radioligand Binding Assay.

Radioligand binding assays were performed at room temperature in 10 mM HEPES/KOH pH 7.4, 1 mM EDTA containing 10 mM $MnCl_2$ and 0.7 nM [$^3$H]$PGD_2$ (NEN, 171 Ci $mmol^{-1}$), in a final volume of 0.2 ml. Competing ligands were diluted in dimethylsulfoxide ($Me_2SO$) that was kept constant at 1% (v/v) of the final incubation volume. The reaction was initiated by the addition of 8-20 μg of membrane protein prepared from a HEK-hCRTH2 cell line. Total and non-specific binding were determined in the absence and the presence of 10 μM $PGD_2$, respectively. Under these conditions, specific binding (total minus non-specific) of the radioligand to the receptor reached equilibrium within 50 min and was stable up to 180 min. The reaction was routinely conducted for 60 min at room temperature and terminated by rapid filtration through prewetted Unifilters GF/C (Packard), using a Tomtec MachIII semi-automated harvester (for HEK-hCRTH2). The filters were then washed with 4 ml of the same buffer and residual radioligand bound to the filter was determined by liquid scintillation counting following equilibration in 25 μl Ultima Gold F™ (Unifilter) (Packard). The compounds of Examples 1-8 have Ki (in nM) values of less than 25 nM.

i[cAMP] Measurements.

HEK-hCRTH2 cells were grown to 80-90% confluency. On the day of the assay, the cells were washed with PBS, incubated for 2 min in cell dissociation buffer, harvested by centrifugation at 300 g for 5 min at room temperature and resuspended at $1.25e10^6$ cells $m^{-1}$ in Hanks' balanced salt solution containing 20 mM HEPES pH 7.4 and 0.75 mM IBMX (HBSS/HEPES/IBMX). The assay was performed in 384-plate format with 0.01 ml HBSS/HEPES/IBMX per well containing 12 500 cells and 75 nl of the test compound at various concentrations. Following a 10 min pre-incubation of the cells with the test compound at 37° C., 0.005 ml of Forskolin/DK-$PGD_2$ dilute in HBSS 20 mM Hepes, was added at a respectively final concentration of 10 uM and 150 nM, to initiate the reaction. After 10 min incubation at 37° C., the cAMP content was quantified using the cAMP XS+HitHunter chemiluminescence assay. (GE Healthcare 90-0075). % inhibition was calculated using the Forskolin and EC85 DK-PGD2 controls.

Eosinophil Shape Change Assay in Human Whole Blood.

Blood was collected in vacutainers containing EDTA. The antagonist was added to blood and incubated for 10 min at room temperature. DK-PGD$_2$ (13,14-dihydro-15-keto prostaglandin D$_2$) was then added to blood for 4 min at 37° C. in a running water bath. Blood cells were then fixed in presence of cold 0.25%(v/v) paraformaldehyde prepared in 75%(v/v) PBS for 1 min on ice. 175 µL of fixed blood was transferred into 870 µL of cold 155 mM NH$_4$Cl lysis solution and incubated at 4° C. for at least 40 min. The solution was then centrifuged at 430 g for 5 min and the supernatant was discarded. Centrifuged cells were analyzed with a FACs Calibur flow cytometer (Becton Dickinson). Flow cytometry raw data were analyzed with FlowJo software by isolating the eosinophils from the neutrophils based on their high autofluorescence and determining the percent of total eosinophils with increased FSC-H value. Maximum (100%) and minimum (0%) shape change were determined in the presence of 10 µM DK-PGD$_2$ and PBS, respectively. A dose response curve with DK-PGD$_2$ was performed with every assay to determine the EC$_{50}$ for each blood donor. Compounds were tested in 10-dose titration curves in the presence of 30 nM DK-PGD$_2$ to determine an antagonist IC$_{50}$.

Some compounds of the present invention are selective for the CRTH2 receptor over the DP receptor. Assays on the DP, as well as other prostanoid, receptors are described in WO2003/06220.

What is claimed is:

1. A compound of the formula I:

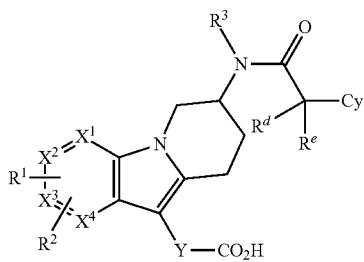

or a pharmaceutically acceptable salt thereof, wherein:
one of $X^1$, $X^2$, $X^3$ and $X^4$ is N and the others are CH;
Y is selected from —C(R$^a$)(R$^b$)—, —C(R$^a$)(R$^b$)—C(R$^a$)(R$^b$)—, —C(R$^a$)=C(R$^b$)—, —OCH$_2$—, —OCH(C$_{1-3}$alkyl)-, —OC(C$_{1-3}$alkyl)$_2$-, —O(CH$_2$)$_{2-5}$—, —SCH$_2$—, —SCH(C$_{1-3}$alkyl)-, —SC(C$_{1-3}$alkyl)$_2$- and —S(CH$_2$)$_{2-5}$—;
Cy is aryl, heteroaryl or C$_{3-6}$ cycloalkyl optionally fused to a benzene, each of which is optionally substituted with 1 to 4 groups independently selected from R$^c$;
R$^1$ is selected from H, halogen, —C$_{1-6}$alkyl and —OC$_{1-6}$alkyl;
R$^2$ is selected from H, halogen, —C$_{1-6}$alkyl, —OC$_{1-6}$alkyl, —SC$_{1-6}$alkyl, —S(O)C$_{1-6}$alkyl, —S(O)$_2$C$_{1-6}$alkyl, —CN, aryl and heteroaryl;
R$^3$ is selected from H, C$_{1-6}$alkyl and benzyl optionally substituted on the phenyl portion with 1 to 3 halogen;
R$^a$ and R$^b$ are independently H, aryl, heteroaryl, C$_{1-6}$alkyl or haloC$_{1-6}$alkyl; or R$^a$ and R$^b$ together with the carbon atom to which they are both attached form a C$_{3-6}$cycloalkyl ring; or
R$^a$ and R$^b$ together with the adjacent carbon atoms to which they are attached form a C$_{3-6}$cycloalkyl ring;
R$^c$ is selected from halogen, NR$^f$R$^g$, SO$_2$NR$^f$R$^g$, CN, C$_{1-6}$alkoxy, C$_{1-6}$alkyl, haloC$_{1-6}$alkoxy, and haloC$_{1-6}$alkyl;
R$^d$ and R$^e$ are independently selected from hydrogen, C$_{1-6}$alkyl, —C$_{1-6}$alkyl-C$_{3-6}$cycloalkyl, hydroxy, C$_{1-6}$alkoxy, aryl optionally substituted with 1 to 3 groups independently selected from R$^c$, and NR$^f$R$^g$; or
R$^d$, R$^e$ together with the carbon atom to which they are both attached form a C$_{3-6}$cycloalkyl optionally having a ring heteroatom selected from —O—, —S—, —N(C(O)R$_f$)— and —N(R$^f$)—, and optionally substituted with 1 to 3 C$_{1-3}$alkyl groups; and
R$^f$ and R$^g$ are independently selected from hydrogen and C$_{1-3}$alkyl; or
R$^f$, R$^g$ together with the atom to which they are both attached form a 3- to 6-membered ring.

2. The compound of claim 1 or a pharmaceutically acceptable salt thereof wherein Cy is phenyl optionally substituted with 1 to 3 groups independently selected from R$^c$.

3. The compound of claim 1 or a pharmaceutically acceptable salt thereof wherein Y is —C(R$^a$)(R$^b$)—.

4. The compound of claim 1 or a pharmaceutically acceptable salt thereof wherein Cy is phenyl optionally substituted with 1 to 2 groups independently selected from halogen, C$_{1-6}$alkyl, haloC$_{1-6}$alkyl and C$_{1-6}$alkoxy.

5. The compound of claim 1 or a pharmaceutically acceptable salt thereof wherein the chiral carbon to which the —NR$^3$—C(O)CR$^d$R$^e$-Cy moiety is attached has the (R)-configuration.

6. The compound of claim 1 I having the formula Ia:

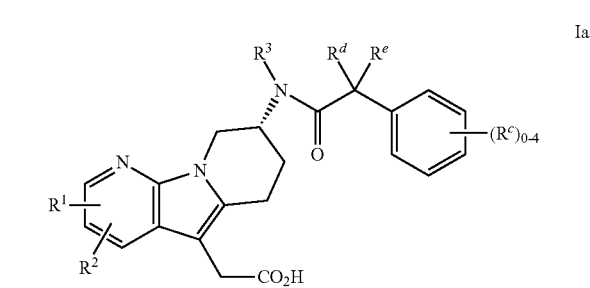

or a pharmaceutically acceptable salt thereof, wherein R$^1$, R$^2$, R$^3$, R$^c$, R$^d$ and R$^e$ are as defined in claim 1.

7. The compound of claim 6 or a pharmaceutically acceptable salt thereof wherein R$^1$ and R$^2$ are each hydrogen.

8. The compound of claim 1 having the formula Ib:

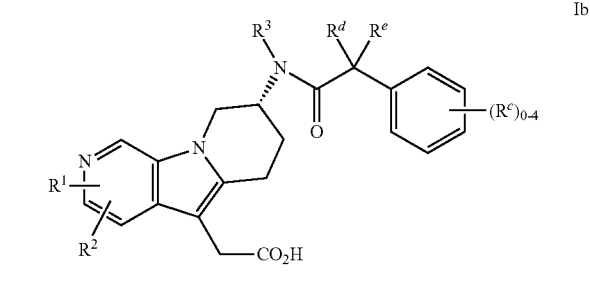

or a pharmaceutically acceptable salt thereof, wherein R$^1$, R$^2$, R$^3$, R$^c$, R$^d$ and R$^e$ are as defined in claim 1.

9. The compound of claim 8 or a pharmaceutically acceptable salt thereof wherein $R^1$ and $R^2$ are each hydrogen.

10. The compound of claim 1 having the formula Ic:

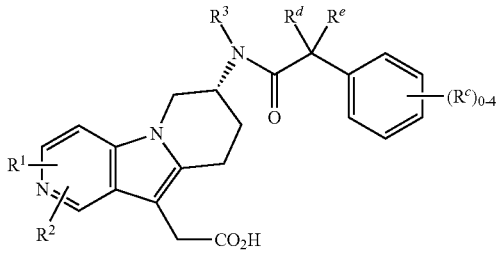

Ic or a pharmaceutically acceptable salt thereof, wherein $R^1$, $R^2$, $R^3$, $R^c$, $R_d$ and $R^e$ are as defined in claim 1.

11. The compound of claim 10 or a pharmaceutically acceptable salt thereof wherein $R^1$ and $R^2$ are each hydrogen.

12. The compound of claim 1 having the formula Id:

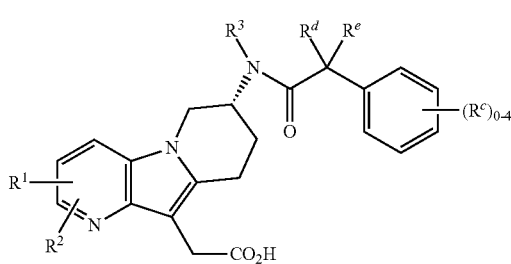

Id or a pharmaceutically acceptable salt thereof, wherein $R^1$, $R^2$, $R^3$, $R^c$, $R^d$ and $R^e$ are as defined in claim 1.

13. The compound of claim 12 or a pharmaceutically acceptable salt thereof wherein $R^1$ and $R^2$ are each hydrogen.

14. The compound of claim 1 having the formula Ie:

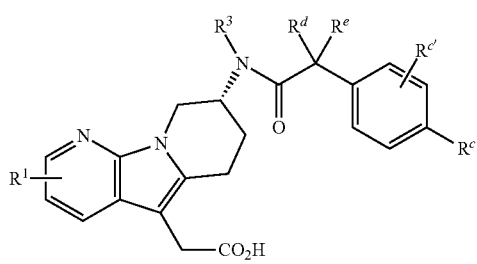

Ie or a pharmaceutically acceptable salt thereof, wherein $R^1$ and $R^3$ are as defined in claim 1; $R^c$ is a halogen; $R^{c'}$ is hydrogen or a halogen; $R^d$ and $R^e$ are independently selected from hydrogen and $C_{1-3}$alkyl, or $R^d$ and $R^e$ together with the carbon atom to which they are both attached form a $C_{3-6}$cycloalkyl or tetrahydropyranyl, each of which is optionally substituted with 1 to 2 $C_{1-3}$alkyl groups.

15. The compound of claim 14 or a pharmaceutically acceptable salt thereof wherein $R^1$ and $R^{c'}$ are each hydrogen, $R^c$ is a fluorine, and $R^3$ is methyl.

16. A compound selected from the group consisting of:
((8R)-8-{methyl[(2R)-2-(4-fluorophenyl)propanoyl]amino}-6,7,8,9-tetrahydropyrido[3,2-b]-indolizin-5-yl)acetic acid;
((8R)-8-{methyl[(2S)-2-(4-fluorophenyl)propanoyl]amino}-6,7,8,9-tetrahydropyrido[3,2-b]-indolizin-5-yl)acetic acid;
{(8R)-8-[[2-(4-fluorophenyl)-3-methylbutanoyl](methyl)amino]-6,7,8,9-tetrahydropyrido[3,2-b]indolizin-5-yl}acetic acid;
{(8R)-8-[(diphenylacetyl)(methyl)amino]-6,7,8,9-tetrahydropyrido[3,2-b]indolizin-5-yl}acetic acid;
{(8R)-8-[[2-(4-fluorophenyl)-2-methylpropanoyl](methyl)amino]-6,7,8,9-tetrahydropyrido[3,2-b]indolizin-5-yl}acetic acid;
{(8R)-8-[{[4-(4-fluorophenyl)tetrahydro-2H-pyran-4-yl]carbonyl}(methyl)amino]-6,7,8,9-tetrahydropyrido[3,2-b]indolizin-5-yl}acetic acid;
{(8R)-8-[{[1-(4-fluorophenyl)-2,2-dimethylcyclopropyl]carbonyl}(methyl)amino]-6,7,8,9-tetrahydropyrido[3,2-b]indolizin-5-yl}acetic acid;
{(8R)-8-[{[1-(4-fluorophenyl)cyclobutyl]carbonyl}(methyl)amino]-6,7,8,9-tetrahydropyrido[3,2-b]indolizin-5-yl}acetic acid; and
{(8R)-8-[{[1-(4-fluorophenyl)cyclopentyl]carbonyl}(methyl)amino]-6,7,8,9-tetrahydro-pyrido[3,2-b]indolizin-5-yl}acetic acid;
or a pharmaceutically acceptable salt thereof.

17. The compound of claim 1 which is ((8R)-8-{methyl[(2R)-2-(4-fluorophenyl)propanoyl]amino}-6,7,8,9-tetrahydropyrido[3,2-b]indolizin-5-yl)acetic acid or a pharmaceutically acceptable salt thereof.

18. The compound of claim 1 which is ((8R)-8-{methyl[(2S)-2-(4-fluorophenyl)propanoyl]amino}-6,7,8,9-tetrahydropyrido[3,2-b]indolizin-5-yl)acetic acid or a pharmaceutically acceptable salt thereof.

19. The compound of claim 1 which is {(8R)-8-[[2-(4-fluorophenyl)-3-methyl-butanoyl](methyl)amino]-6,7,8,9-tetrahydropyrido[3,2-b]indolizin-5-yl}acetic acid or a pharmaceutically acceptable salt thereof.

20. The compound of claim 1 which is {(8R)-8-[(diphenylacetyl)(methyl)amino]-6,7,8,9-tetrahydropyrido[3,2-b]indolizin-5-yl}acetic acid or a pharmaceutically acceptable salt thereof.

21. The compound of claim 1 which is {(8R)-8-[[2-(4-fluorophenyl)-2-methyl-propanoyl] (methyl)amino]-6,7,8,9-tetrahydropyrido[3,2-b]indolizin-5-yl}acetic acid or a pharmaceutically acceptable salt thereof.

22. The compound of claim 1 which is {(8R)-8-[{[4-(4-fluorophenyl)-tetrahydro-2H-pyran-4-yl]carbonyl}(methyl)amino]-6,7,8,9-tetrahydropyrido[3,2-b]indolizin-5-yl}acetic acid or a pharmaceutically acceptable salt thereof.

23. The compound of claim 1 which is {(8R)-8-[{[1-(4-fluorophenyl)-2,2-dimethylcyclopropyl]carbonyl}(methyl)amino]-6,7,8,9-tetrahydropyrido[3,2-b]indolizin-5-yl}acetic acid or a pharmaceutically acceptable salt thereof.

24. The compound of claim 1 which is {(8R)-8-[{[1-(4-fluorophenyl)-cyclobutyl]carbonyl}(methyl)amino]-6,7,8,9-tetrahydropyrido[3,2-b]indolizin-5-yl}acetic acid or a pharmaceutically acceptable salt thereof.

25. The compound of claim 1 which is {(8R)-8-[{[1-(4-fluorophenyl)-cyclopentyl]carbonyl}(methyl)amino]-6,7,8,9-tetrahydropyrido[3,2-b]indolizin-5-yl}acetic acid or a pharmaceutically acceptable salt thereof.

26. A pharmaceutical composition comprising a therapeutically effective amount of the compound of claim 1 or a pharmaceutically acceptable salt thereof and a pharmaceutically acceptable carrier.

27. The pharmaceutical composition of claim 26 comprising a second active ingredient selected from the group consisting of a leukotriene antagonist, a 5-lipooxygenase inhibitor and a FLAP inhibitor.

* * * * *